United States Patent
Erkamp et al.

(10) Patent No.: US 11,331,070 B2
(45) Date of Patent: May 17, 2022

(54) SYSTEM AND METHOD FOR PROBE CALIBRATION AND INTERVENTIONAL ACOUSTIC IMAGING

(71) Applicant: KONINKLIJKE PHILIPS N.V., Eindhoven (NL)

(72) Inventors: Ramon Quido Erkamp, Swampscott, MA (US); Man Nguyen, Melrose, MA (US); Jean-Luc Robert, Cambridge, MA (US); Sheng-Wen Huang, Ossining, NY (US); Shyam Bharat, Arlington, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 16/066,082

(22) PCT Filed: Dec. 21, 2016

(86) PCT No.: PCT/EP2016/082045
§ 371 (c)(1),
(2) Date: Jun. 26, 2018

(87) PCT Pub. No.: WO2017/114701
PCT Pub. Date: Jul. 6, 2017

(65) Prior Publication Data
US 2019/0008476 A1  Jan. 10, 2019

Related U.S. Application Data

(60) Provisional application No. 62/273,667, filed on Dec. 31, 2015.

(30) Foreign Application Priority Data

Feb. 25, 2016 (EP) .................................. 16157457

(51) Int. Cl.
A61B 8/08 (2006.01)
A61B 8/00 (2006.01)
(Continued)

(52) U.S. Cl.
CPC .......... *A61B 8/0841* (2013.01); *A61B 8/4455* (2013.01); *A61B 8/4483* (2013.01);
(Continued)

(58) Field of Classification Search
CPC ... A61B 8/0841; A61B 8/4483; A61B 8/4455; A61B 8/4488; A61B 8/469;
(Continued)

(56) References Cited

U.S. PATENT DOCUMENTS 4,029,084 A    6/1977 Soldner
4,407,294 A *  10/1983 Vilkomerson ..... A61B 1/00142
                                              600/461
(Continued)

FOREIGN PATENT DOCUMENTS

CN    1764849 A    4/2006
CN    1839769 A    10/2006
(Continued)

*Primary Examiner* — Serkan Akar
*Assistant Examiner* — Renee C Langhals

(57) ABSTRACT

A system includes an acoustic probe and an acoustic imaging machine. The acoustic probe includes a substrate with first and second principal surfaces, a device insertion port with an opening passing through the substrate from the first principal surface to the second principal surface, and an array of acoustic transducer elements supported by the substrate and disposed around the device insertion port. The acoustic imaging machine may systematically vary the size and/or position of the active acoustic aperture of the probe by providing transmit signals to selected acoustic transducer elements to cause the array to transmit an acoustic probe signal to an area of interest and may record a feedback signal
(Continued)

of the transmit signals from an acoustic receiver provided at a distal end of an interventional device passed through the device insertion port into the area of interest to find an active acoustic aperture having optimal acoustic performance.

12 Claims, 14 Drawing Sheets

(51) Int. Cl.
    *G01S 15/89* (2006.01)
    *G01S 7/52* (2006.01)
(52) U.S. Cl.
    CPC ............ *A61B 8/4488* (2013.01); *A61B 8/469* (2013.01); *A61B 8/5269* (2013.01); *G01S 7/52049* (2013.01); *G01S 15/8915* (2013.01); *G01S 15/8927* (2013.01)
(58) Field of Classification Search
    CPC ......... A61B 8/5269; A61B 8/54; A61B 8/444; G01S 15/8927; G01S 7/52049; G01S 15/8915
    USPC ........................................................ 600/424
    See application file for complete search history.

(56) References Cited

U.S. PATENT DOCUMENTS

| | | | |
|---|---|---|---|
| 5,448,997 A * | 9/1995 | Kruse | A61N 1/3702 600/510 |
| 7,529,393 B2 | 5/2009 | Peszynski et al. | |
| 8,792,295 B2 | 7/2014 | Kristoffersen et al. | |
| 2003/0060700 A1 | 3/2003 | Solf et al. | |
| 2005/0101868 A1 | 5/2005 | Ridley et al. | |
| 2006/0241489 A1 | 10/2006 | Hiki et al. | |
| 2012/0157849 A1* | 6/2012 | Ridley | A61B 8/4444 600/443 |
| 2013/0041252 A1 | 2/2013 | Vignon et al. | |
| 2013/0096430 A1 | 4/2013 | Yoshiara et al. | |
| 2014/0043933 A1* | 2/2014 | Belevich | A61B 8/4488 367/11 |
| 2014/0148701 A1* | 5/2014 | Yao | A61B 8/4254 600/447 |
| 2014/0243668 A1 | 8/2014 | Varghese et al. | |
| 2015/0065871 A1* | 3/2015 | Konofagou | A61B 8/4281 600/431 |
| 2015/0157294 A1* | 6/2015 | Smith | A61B 8/5207 600/447 |
| 2016/0074016 A1* | 3/2016 | Park | G10K 11/346 600/459 |
| 2016/0242856 A1 | 8/2016 | Jain et al. | |

FOREIGN PATENT DOCUMENTS

| | | |
|---|---|---|
| CN | 101467896 A | 7/2009 |
| CN | 103222897 A | 7/2013 |
| CN | 103284754 A | 9/2013 |
| CN | 103747743 A | 4/2014 |
| CN | 104411251 A | 3/2015 |
| CN | 105073016 A | 11/2015 |
| JP | H0643242 A | 2/1994 |
| JP | H0928708 A | 2/1997 |
| JP | 2002511781 A | 4/2002 |
| JP | 2011104052 A | 6/2011 |
| JP | 2013081764 A | 5/2013 |
| JP | 2013240507 A | 12/2013 |
| JP | 2015226572 A | 12/2015 |
| WO | 9847428 A1 | 10/1998 |
| WO | 2007073551 A1 | 6/2007 |
| WO | 2013005123 A1 | 1/2013 |
| WO | 2014002066 A3 | 1/2014 |
| WO | 2014138050 A1 | 9/2014 |

\* cited by examiner

SYSTEM AND METHOD FOR PROBE CALIBRATION AND INTERVENTIONAL ACOUSTIC IMAGING

This application is the U.S. National Phase application under 35 U.S.C. § 371 of International Application No. PCT/EP2016/082045, filed on Dec. 21, 2016, which claims the benefit of Provisional Application Ser. No. 62/273,667, filed Dec. 31, 2015 and EP Application Ser. No. 16157457.9 filed Feb. 25, 2016. These applications are hereby incorporated by reference herein.

TECHNICAL FIELD

This invention pertains to acoustic (e.g., ultrasound) imaging, and in particular a system and method for acoustic imaging in conjunction with an interventional procedure.

BACKGROUND

Acoustic (e.g., ultrasound) imaging systems are increasingly being employed in a variety of applications and contexts. For example, ultrasound imaging is being increasingly employed in the context of minimally invasive surgeries. This includes needle based procedures such as Chorionic Villus Sampling (CVS), needle based biopsies, and nerve blocks for local anesthesia. Today, typically the imaging probes that are used in minimally invasive interventional procedures have an imaging array configuration that is identical to that of the probes used in diagnostic imaging.

Visualization of an interventional device, or devices, (e.g., surgical instrument(s)) employed in these procedures using existing acoustic probes and imaging systems is challenging in many cases, and often requires manual repositioning of the acoustic probe during the procedure to maintain sufficient image quality. A significant percentage of CVS procedures are described by the physician as difficult, and an even greater percentage are reported to have involved more than one insertion.

To address these problems, special interventional devices, such as echogenic needles, with enhanced visibility are successfully on the market and provide limited improvement at moderate extra cost. More progress in needle visualization has recently been made in the form of needle tracking technologies, based on magnetic tracking or stereoscopic cameras with optical fiducials. These visualization techniques could also be applied to other interventional devices Even with these improvements, certain clinical applications (e.g., deep nerve block) still remain largely or completely out of reach because of certain limitations to existing acoustic imaging probes and systems. In many cases, anatomical features at the intervention site cannot be sufficiently resolved, especially for procedures which are performed at greater depths beneath the skin surface. For example, acoustic imaging guidance is used in shallow nerve blocks (e.g., up to depths of 3 cm) and is able to visualize the nerves in such procedures. Acoustic imaging is also employed for deep nerve, but because existing systems cannot visualize these nerves, physicians use anatomical landmarks as guidance, making deep blocks much harder to perform. Instrument visualization also can be poor due to specular reflection of device surface. Furthermore, during ultrasound guided interventional procedures, one does not want to have to manipulate the position of the imaging probe.

Clearly there are already many existing applications for interventional ultrasound, and additional applications could be realized with improvements in device and anatomy visualization and in operating characteristics. Such applications may include cancer ablation procedures, CVS, fetal surgeries/interventions (e.g., altering blood flow patterns in twin-to-twin transfusion syndrome (TTTS)), liver biopsies, and deep nerve block procedures.

Desirable attributes for an acoustic imaging system and method include: accurate visualization of the instrument in the ultrasound image; enhanced imaging resolution at the location of intervention; and hands free operation of the acoustic probe.

Accordingly, it would be desirable to provide an ultrasound system, an acoustic probe, and a method which can provide enhanced acoustic imaging capabilities during interventional procedures. It is known to include a device insertion port into an ultrasound probe such that an interventional device can be inserted through the device insertion port and imaged using the ultrasound probe. This for example is disclosed in US 2014/0148701 A1. WO 2011/138698 A1 furthermore teaches that an interventional tool such as a catheter may have an ultrasound receiver to aid determination of the position of the tool with an ultrasound probe.

In order to improve the anatomical feature visualization with such ultrasound imaging systems, large area ultrasound probes have been devised, e.g. probes having an active area with a diameter of at least 10 cm, such that these probes have a particularly large active coherent aperature size. Such probes may be conformable to a body surface to facilitate imaging of a large anatomical area of interest. However, in such applications it is often the case that the large size of the active area causes aberration and refraction artefacts in the captured ultrasound images. Hence, there exists a need for a system including such a large area probe that can deliver improved quality ultrasound images.

SUMMARY

The present invention seeks to provide a system that can deliver acoustic images of sufficient quality even when a large area ultrasound probe is used.

The present invention further seeks to provide a method for delivering such acoustic images.

In one aspect of the invention, a system comprises: an acoustic probe having: a substrate having first and second principal surfaces, and further having at least one device insertion port comprising an opening passing through the substrate from the first principal surface to the second principal surface, and an array of acoustic transducer elements supported by the substrate and disposed around the at least one device insertion port; and an acoustic imaging machine connected to the acoustic probe and configured to systematically vary a selection of the acoustic transducer elements, and, for each selection, provide transmit signals to the selection of the acoustic transducer elements to cause the selection of acoustic transducer elements to transmit an acoustic probe signal to the area of interest; and record a feedback signal of the transmit signals from an acoustic receiver provided at a distal end of the interventional device passed through the device insertion port into the area of interest; the acoustic imaging machine being further configured to evaluate the recorded feedback signals to identify a preferred selection of the acoustic transducer elements; transmit further signals to the preferred selection of the acoustic transducer elements to cause the preferred selection of acoustic transducer elements to transmit a further acoustic probe signal to the area of interest; and produce acoustic images of the area of interest from acoustic echoes received by the acoustic probe from the area of interest in response to said further acoustic probe signal.

In accordance with the present invention, the acoustic imaging machine is configured to dynamically determine the optimum size and/or position of the active aperture of the ultrasound probe, i.e. the number and/or the position of acoustic transducer elements to be engaged in the generation of the acoustic images with the aid of the interventional device, such that the acoustic imaging machine may produce acoustic images of an area of interest including the interventional device having an optimized image quality.

The acoustic imaging machine may be configured to evaluate the recorded feedback signals to identify the preferred selection of the acoustic transducer elements using a metric for assessing a focal point quality of the transmit signals onto the acoustic receiver for each of said selections. The metric used may depend from the clinical application. For example, the metric may be for minimizing sidelobe energy if small hypo-echoic features are important or may be for maximizing main lobe definition if small hyper-echoic features require resolving.

Each selection may define an active aperture of the acoustic probe, wherein the acoustic acoustic imaging machine may be configured to systematically vary the selection of the acoustic transducer elements by systematic variation of at least one of a location of the active aperture and a size of the active aperture in order to obtain the optimal active aperture of the ultrasound probe in its target application.

In a preferred embodiment, the acoustic imaging machine is configured to systematically vary the selection of the acoustic transducer elements by repeatedly systematically varying a location of the active aperature having a defined size; and redefining the size of the active aperature based on a defined range of sizes for the acoustic aperature until each size in said defined range of sizes has been used in order to obtain this optimal active aperture.

The acoustic imaging machine further may be configured to systematically vary a beam steering angle for each selection of the of the acoustic transducer elements during the systematic variation of the selection of the acoustic transducer elements. In this embodiment, the electronic beam steering may take the place of varying the location of the active aperture during the selection process, which may reduce the duration of this process.

In some versions of these embodiments, the acoustic imaging machine is further configured to use the feedback signal from the acoustic receiver to register a location of the acoustic receiver with respect to the acoustic echoes received by the acoustic probe, and to use the registration to mitigate aberration artifacts in the acoustic images In some embodiments, the substrate has a shape of a concave disc, and wherein an active area of the substrate defined by the array of acoustic transducer elements has a diameter of at least approximately 12 cm.

In some versions of these embodiments, the system is configured to provide an active acoustic aperture at a given time of at least 10 cm.

In some versions of these embodiments, the center frequency of the acoustic probe signal is about 3.5 MHz, and wherein at least some of the acoustic transducer elements have a size which is approximately 0.44 mm.

In another aspect of the invention, a method comprises: providing an acoustic probe comprising a substrate configured to be applied to the skin of a subject, the substrate having first and second principal surfaces and further having at least one device insertion port comprising an opening passing through the substrate from the first principal surface to the second principal surface, and an array of acoustic transducer elements supported by the substrate and disposed around the at least one device insertion port; systematically varying a selection of the acoustic transducer elements, and, for each selection, providing transmit signals to the selection of the acoustic transducer elements to cause the selection of acoustic transducer elements to transmit an acoustic probe signal to the area of interest and recording a feedback signal of the transmit signals from an acoustic receiver provided at a distal end of an interventional device passed through the device insertion port into the area of interest; evaluating the recorded feedback signals to identify a preferred selection of the acoustic transducer elements; transmitting further signals to the preferred selection of the acoustic transducer elements to cause the preferred selection of acoustic transducer elements to transmit a further acoustic probe signal to the area of interest; and producing acoustic images of the area of interest from acoustic echoes received by the acoustic probe from the area of interest in response to said further acoustic probe signal.

With this method, the size and/or position of the active aperture of the ultrasound probe relative to the interventional device may be optimized in terms of image quality to support acoustic imaging of an interventional procedure with the acoustic probe. It is noted for the sake of completeness that the insertion of the interventional device into the area of interest does not form part of the claimed invention, which typically takes place after the interventional device has been inserted.

In an embodiment, evaluating the recorded feedback signals to identify the preferred selection of the acoustic transducer elements comprises using a metric for assessing a focal point quality of the transmit signals onto the acoustic receiver for each of said selections. It has been found that this is a reliable metric for determining the image quality of acoustic images to be generated with such a selection of acoustic transducer elements.

As previously explained, each selection may define an active aperture of the acoustic probe, wherein systematically varying the selection of the acoustic transducer elements may comprise systematically varying at least one of a location of the active aperture and a size of the active aperture in order to determine the preferred selection of acoustic transducer elements to define the active aperture of the acoustic probe. This preferably comprises repeatedly systematically varying a location of the active aperature having a defined size; and redefining the size of the active aperature based on a defined range of sizes for the acoustic aperature until each size in said defined range of sizes has been used.

In an embodiment, the method further comprises varying a beam steering angle for each selection of the of the acoustic transducer elements during the systematic variation of the selection of the acoustic transducer elements. This at least under certain conditions may obviated the need to relocate the active aperture, thereby reducing the time required for the active aperture determination process.

The method may further comprise using the feedback signal from the acoustic receiver to register a location of the acoustic receiver with respect to the acoustic echoes received by the acoustic probe; and using the registration of the location of the acoustic receiver with respect to the acoustic echoes to mitigate aberration artifacts in the acoustic images to further improve the image quality of the acoustic images obtained with the ultrasound probe.

Furthermore, the method may further comprise repeating the systematic variation of a selection of the acoustic transducer elements and the evaluation of the recorded feedback signals to identify a preferred selection of the acoustic transducer elements in response to a change in position of the interventional device within the area of interest. Because the optimal active aperture may change as a function of the position of the interventional device within the area of interest, this ensures that the active aperture remains optimized upon a change in this position.

In some embodiments, the center frequency of the acoustic probe signal is about 3.5 MHz, and wherein the area of interest includes an area about 8 cm beneath the skin.

In some versions of these embodiments, the method further comprises the acoustic probe selectively allowing the interventional device to move freely within the device insertion port, and locking the interventional device within the device insertion port, in response to a user input via a user interface associated with the acoustic probe.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. Herein, when something is said to be "approximately" or "about" a certain value, it means within 10% of that value.

Figure 1:
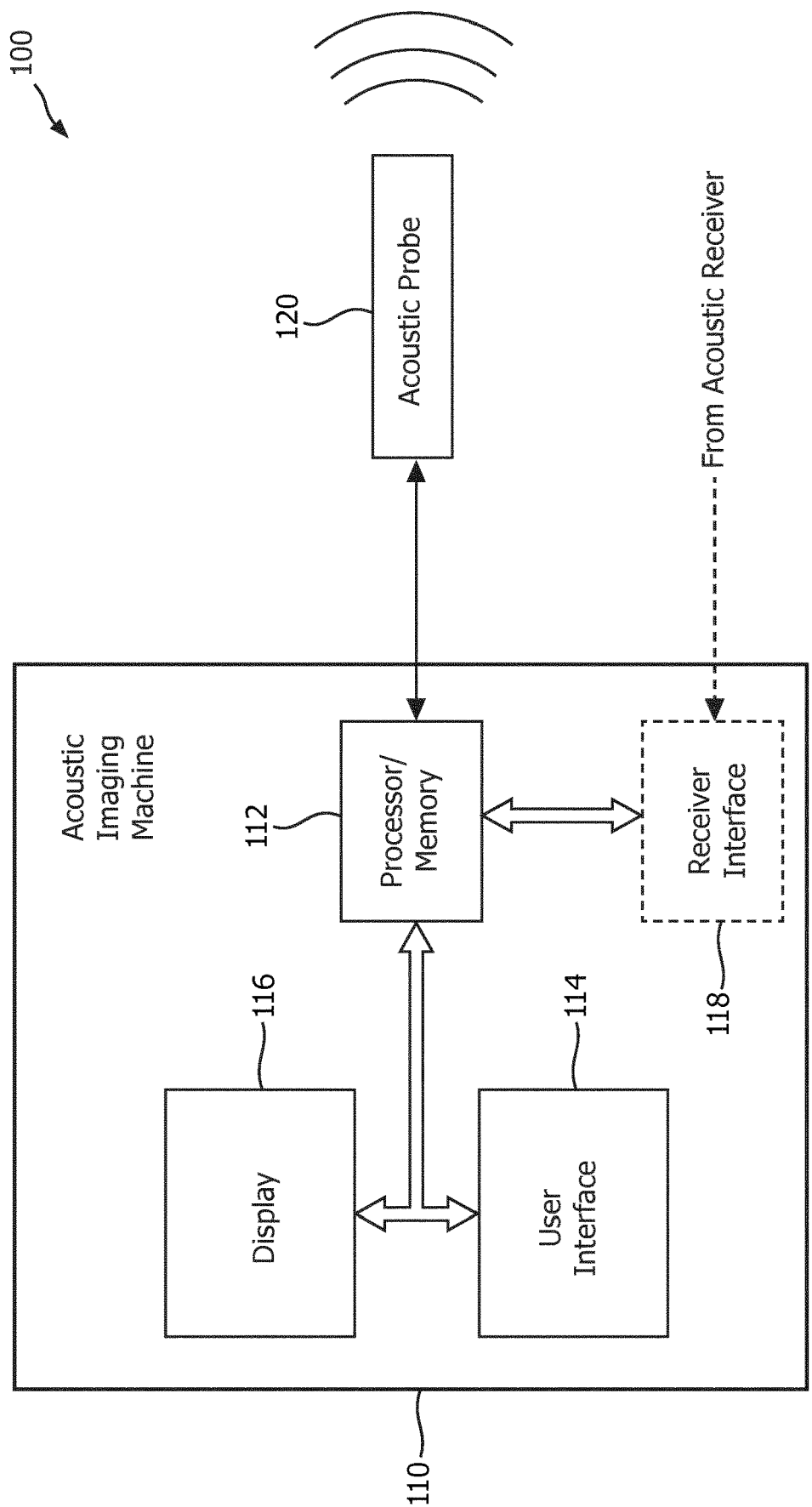
FIG. 1 shows one example of a system with an acoustic imaging machine and an acoustic probe.

FIG. 1 shows one example of an acoustic imaging system 100 which includes an acoustic imaging machine 110 and an acoustic probe 120. Acoustic imaging machine 110 include a processor (and associated memory) 112, a user interface 114, a display 116 and optionally a receiver interface 118.

In various embodiments, processor 112 may include various combinations of a microprocessor (and associated memory), a digital signal processor, an application specific integrated circuit (ASIC), a field programmable gate array (FPGA), digital circuits and/or analog circuits. Memory (e.g., nonvolatile memory) associated with processor 112 may store therein computer-readable instructions which cause a microprocessor of processor 112 to execute an algorithm to control system 100 to perform one or more operations or methods which are described in greater detail below. In some embodiments, a microprocessor may execute an operating system. In some embodiments, a microprocessor may execute instructions which present a user of system 100 with a graphical user interface (GYI) via user interface 114 and display 116.

In various embodiments, user interface 114 may include any combination of a keyboard, keypad, mouse, trackball, stylus/touch pen, joystick, microphone, speaker, touchscreen, one or more switches, one or more knobs, one or more lights, etc. In some embodiments, a microprocessor of processor 112 may execute a software algorithm which provides voice recognition of a user's commands via a microphone of user interface 114.

Display device 116 may comprise a display screen of any convenient technology (e.g., liquid crystal display). In some embodiments the display screen may be a touchscreen device, also forming part of user interface 114.

In some embodiments, acoustic imaging machine 110 may include receiver interface 118 which is configured to receive one or more electrical signals from an external acoustic receiver, for example an acoustic receiver disposed at or near a distal end (tip) of an interventional device, as will be described in greater detail below, particularly with respect to FIG. 4.

Of course it is understood that acoustic imaging machine 110 may include a number of other elements not shown in FIG. 1, for example a power system for receiving power from AC Mains, an input/output port for communications between processor 112 and acoustic probe 120), a communication subsystem for communicating with other eternal devices and systems (e.g., via a wireless, Ethernet and/or Internet connection), etc.

Figure 2A:
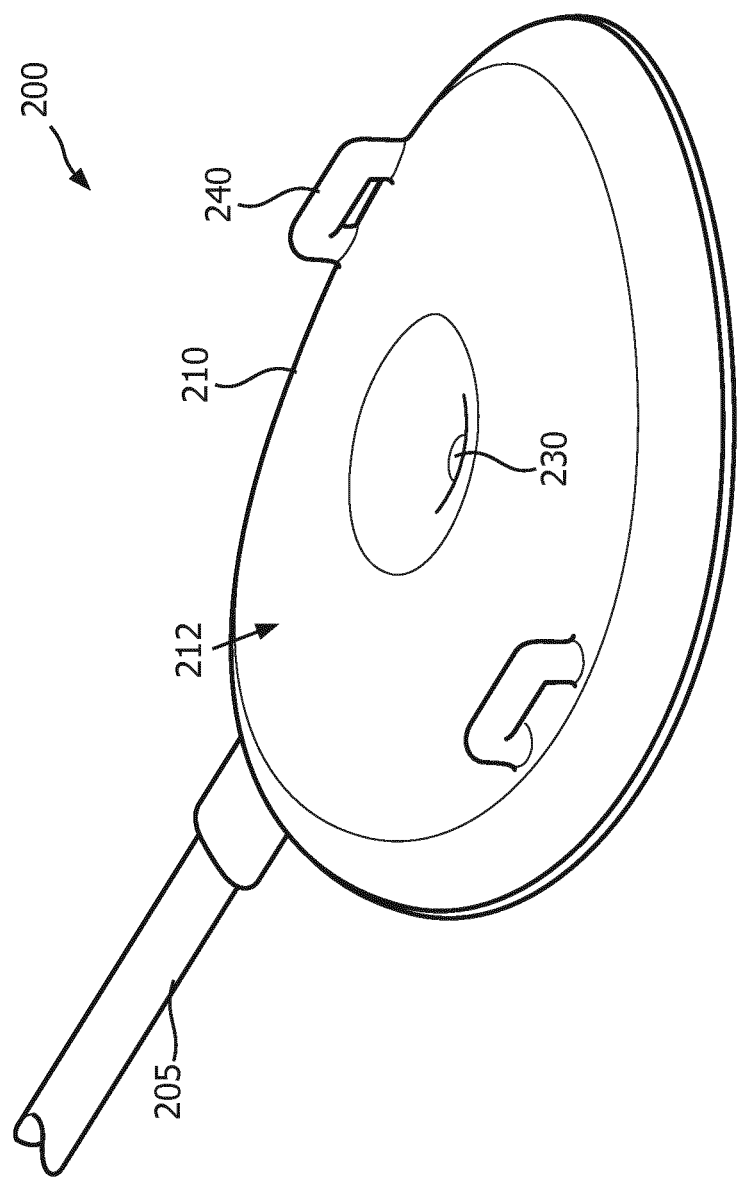
FIGS. 2A and 2B illustrate one example embodiment of an acoustic probe.
Figure 2B:
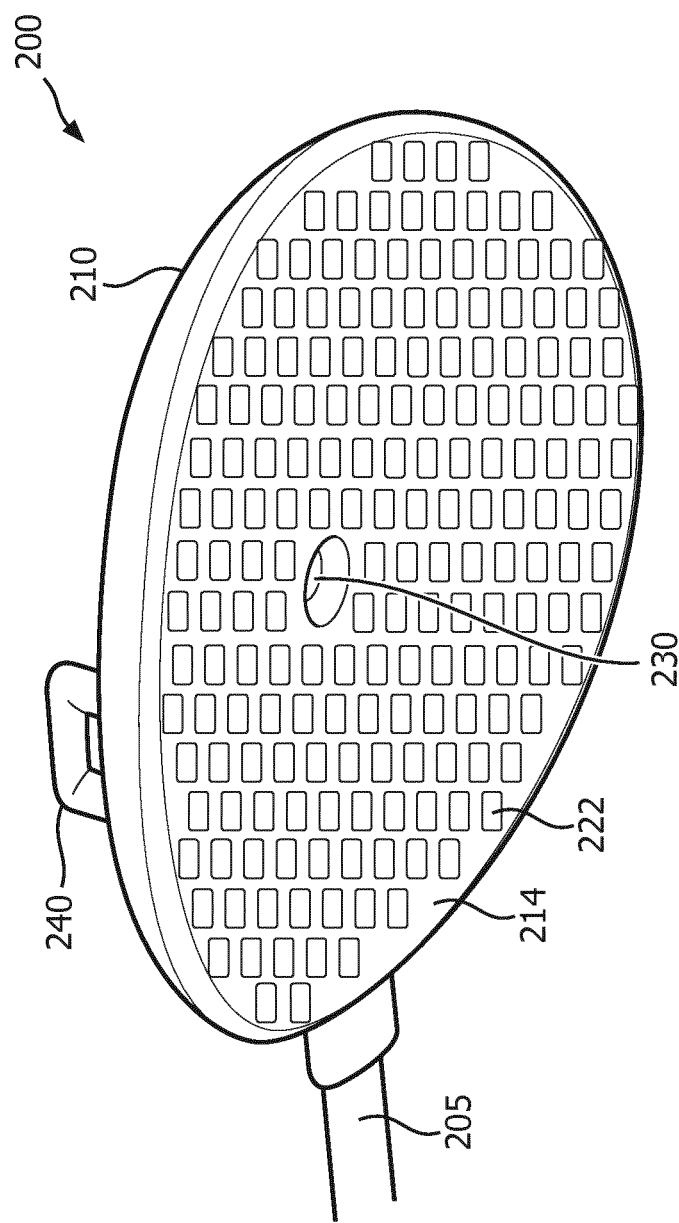

FIGS. 2A and 2B illustrate one example embodiment of an acoustic probe 200. Acoustic probe 200 may be one embodiment of acoustic probe 120 in system 100.

Acoustic probe 200 includes a substrate 210 having first and second principal surfaces 212 and 214, and further having a device insertion port 230 comprising an opening passing through substrate 210 from first principal surface 212 to second principal surface 214. Acoustic probe 200 also includes an array of acoustic transducer elements 222 supported by substrate 210 and disposed around device insertion port 230.

Acoustic probe 200 optionally includes a pair of hooks or attachments 240 which may be used for attaching an elastic strap (e.g., via Velcro) which can go around the back of the subject to attach acoustic probe 200 to the subject.

Associated with acoustic probe 200 may be a side-mounted flat probe cable 205 which can be taped to a subject's skin during an ultrasound imaging examination of the subject, to help in further stabilizing the position of acoustic probe 200. The other end of probe cable 205 may be attached to an acoustic imaging machine (e.g., acoustic imaging machine 110 of FIG. 1) for communicating electrical signals between acoustic probe 120 and the acoustic imaging system.

Beneficially acoustic probe 200, and in particular substrate 210, including first and second principal surfaces 212 and 214, has a form factor or shape of a disc that is concavely curved to fit a subject's abdominal anatomy. The acoustic probe 200 may be flexible to a degree in order to more snugly fit the subject's abdominal anatomy.

Device insertion port 230 is configured to accommodate an interventional device (e.g., surgical instrument) to pass therethrough from first principal surface 212 to second principal surface 214 and then into a subject's body at a treatment site.

Figure 3:
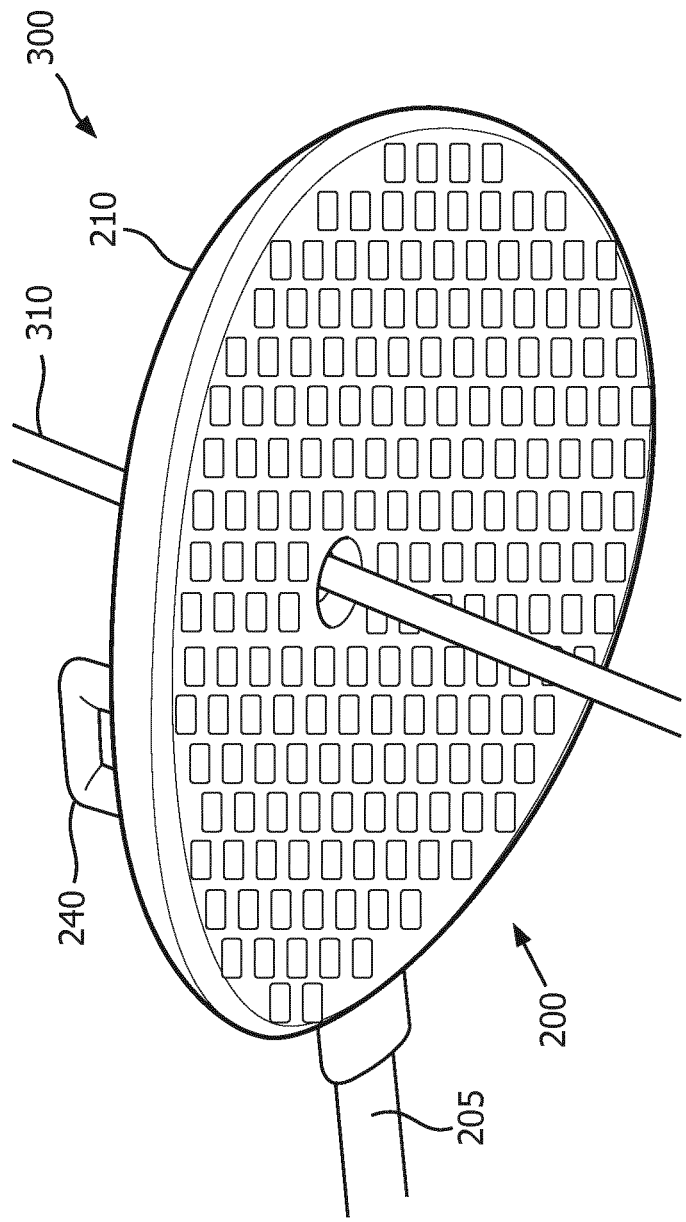
FIG. 3 illustrates example embodiment of an acoustic probe and an interventional device passing through a device insertion port in the acoustic probe.

FIG. 3 illustrates example embodiment of an arrangement 300 of acoustic probe 200 and an interventional device 310 passing through device insertion port 230 of acoustic probe 200. In some embodiments, device insertion port 230 may have a size such that an interventional device 310 having a diameter of 1 cm can pass therethrough.

Although acoustic probe 200 includes a single device insertion port 230, in other embodiments an acoustic probe may include two or more device insertion port(s) 230. Also, although in acoustic probe 200 device insertion port 230 has a generally circular shape and is disposed at a center of substrate 210, in other embodiments a device insertion port may have a different shape and/or may be located in a different place on the substrate.

Figure 4:
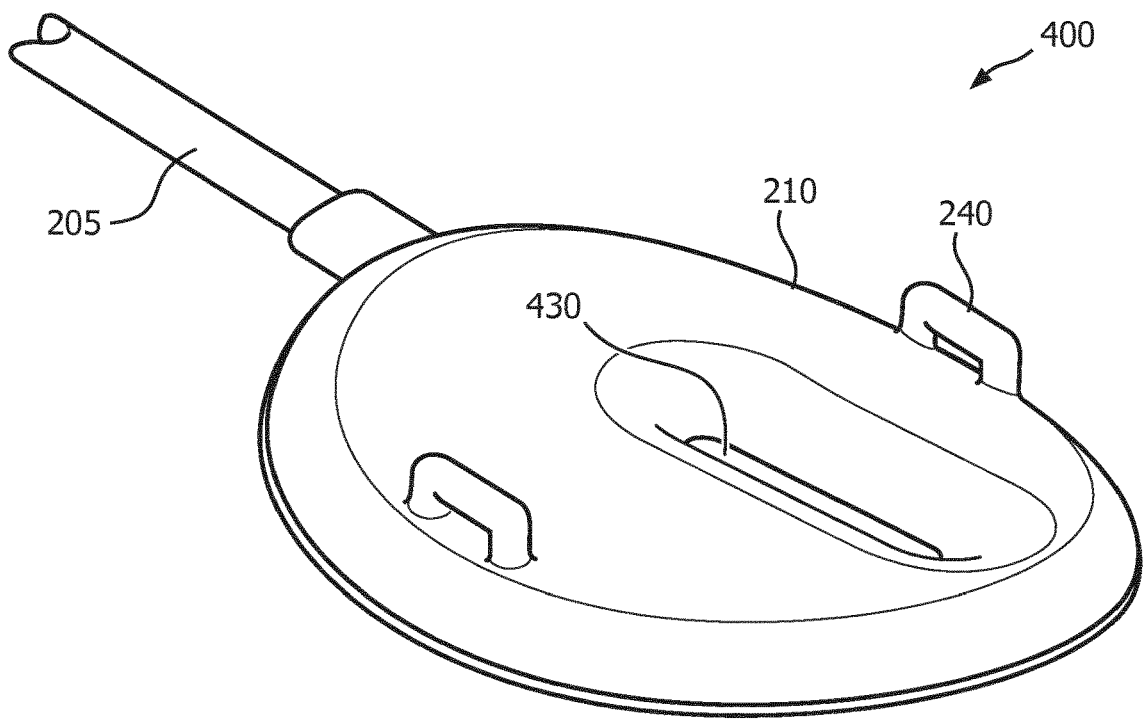
FIG. 4 illustrates another example embodiment of an acoustic probe.
Figure 5:
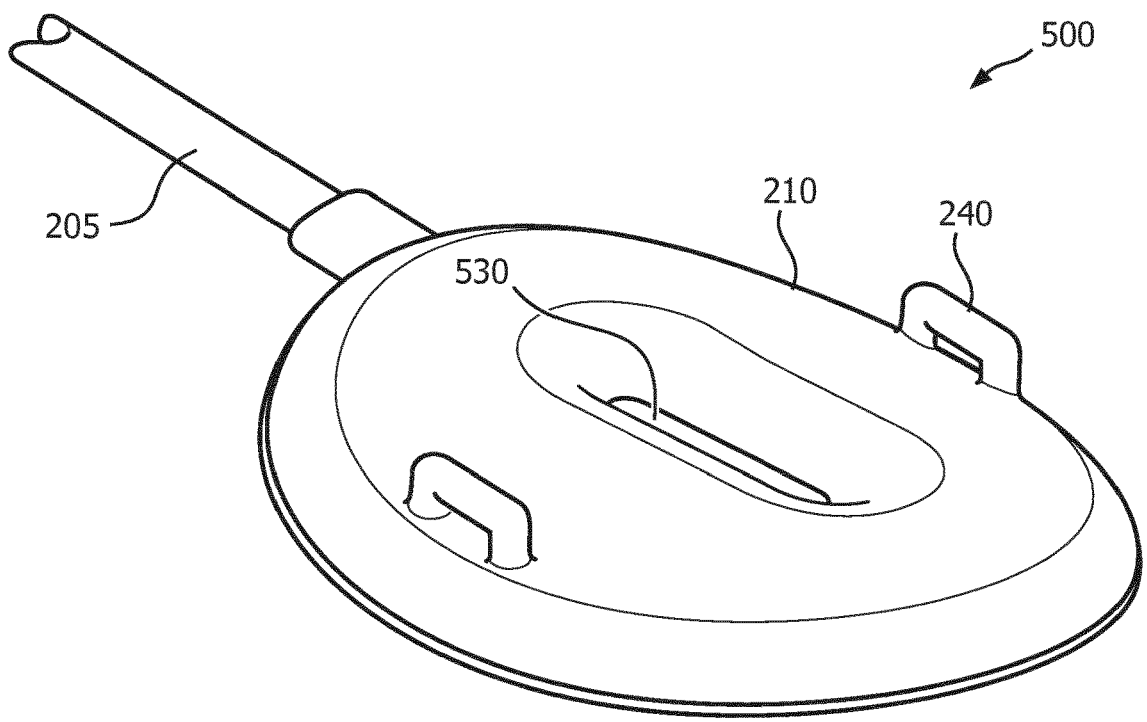
FIG. 5 illustrates yet another example embodiment of an acoustic probe.

For example, FIG. 4 illustrates another example embodiment of an acoustic probe 400 which includes a device insertion port 430 having the shape of an elongated radial slit or slot, instead of a small hole in the center of substrate 210 which only offers a single fixed skin entry point once acoustic probe 200 is fixed to the subject. Elongated radial slot 430 may provide more flexibility for finding a suitable skin insertion point and trajectory for inserting an interventional device into the subject's tissue without having to reposition acoustic probe 400. FIG. 5 illustrates yet another example embodiment of an acoustic probe 500 with a device insertion port 530 having the shape of an elongated slit or slot. In other embodiments, an acoustic probe may include a plurality of elongated slits or slots extending radially from the center of substrate 210. In other embodiments, an acoustic probe may include one or more device insertion ports having the shape of "x-shaped" slots or slits which may allow an interventional device to be moved in two (e.g., orthogonal) directions within the insertion port to reach a desired insertion location.

The acoustic probe 200 (and acoustic probes 400 and 500) comprises a large transducer array with an imaging aperture which surrounds the insertion location of the interventional device. For example, in some versions, an active area of substrate 210 defined by the array of acoustic transducer elements 222 may have a diameter of at least approximately 12 cm. Beneficially, substrate 210 may have a thickness of approximately 1 cm. Beneficially, substrate 210 may be rigid or semi-rigid. It will be understood that other dimensions are of course equally feasible, for example depending on clinical application domain.

Some versions of acoustic probe 200 may be employed for abdominal interventions at depths of approximately 8 cm. Interventions that fall in this category may include Chorionic Villus Sampling and fetal interventions such as altering blood flow patterns in twin-to-twin transfusion syndrome (TTTS). Some versions of acoustic probe 200 may be used with an acoustic imaging machine (e.g., acoustic imaging machine 110) to resolve nerve fibers at 8 cm depth.

Operationally, to get sufficient signal at 8 cm depth, the ultrasound center frequency of system 100 may be chosen sufficiently low, for example approximately 3.5 MHz or less. Beneficially, in a case where the region of interest is known to be close to 8 cm deep and located relatively close to the central axis of the array of acoustic transducer elements 222, only small steering angles may be required. In this case, the size of acoustic transducer elements 222 may be relatively large and acoustic probe 200 may be operated in a manner similar to a linear array.

Beneficially, acoustic transducer elements 222 have a size of about one wavelength, for example about 0.44 mm when acoustic probe is controlled by an acoustic imaging machine to operate at about 3.5 MHz. In that case, in some versions acoustic probe 200 may have about 60000 acoustic transducer elements populating substrate 210 surrounding device insertion port 230.

If acoustic probe 200 is used with a system (e.g., system 100) which allows tracking, then acoustic imaging machine 110 knows the position of the interventional device tip and may only need to image a small area of interest around this tip. In some embodiments, tracking could be done by providing a passive acoustic receiver at or near a distal end of interventional device 300 passing through device insertion port 230 of acoustic probe 200 in the area of interest.

Figure 6:
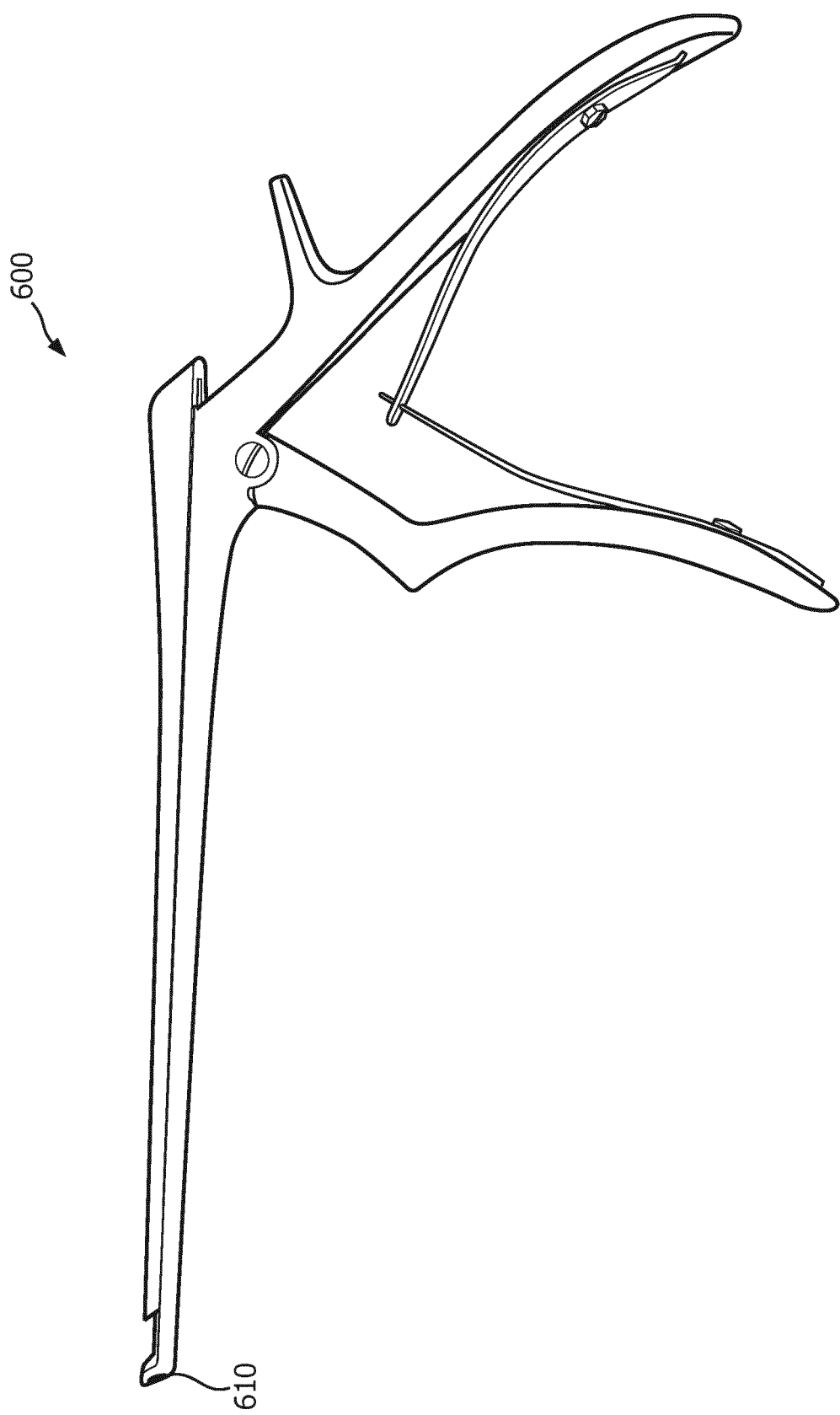
FIG. 6 illustrates one example embodiment of an interventional device having an acoustic receiver disposed at a distal end thereof.

FIG. 6 illustrates one example embodiment of an interventional device 600 having an acoustic receiver (e.g., a passive acoustic receiver) 610 disposed at a distal end thereof. Interventional device 600 may be one embodiment of interventional device 300, and accordingly may be configured to pass through device insertion port 230 of acoustic probe 200. Although only one acoustic receiver 610 is shown for interventional device 600, other embodiments of interventional devices may include two or more acoustic receiver(s) 610.

For real-time guidance of an interventional device employed in an interventional procedure, in some cases it may be sufficient to only image an area of interest comprising a 2×2 cm X-plane at the tip of interventional device 600. This may be achieved by creating an active acoustic aperture of at least approximately 10 cm at any given time, and sliding it over a 2 cm range in lateral and elevational directions over time. The active aperture of the array is defined by the area of the transducers, which are simultaneously activated at the given moment of time for the transmission event.

However, such a large active aperture is, in general, susceptible to aberration artifacts as has been explained in more detail above. Beneficially, in some embodiments such artifacts may be mitigated by processor 112 of acoustic imaging machine 110 using feedback received by receiver interface 118 from one or more passive acoustic receivers 610 on interventional device 600.

With proper aberration correction, this may allow imaging at about twice the depth of a conventional acoustic probe without sacrificing imaging resolution. In general, imaging at twice the depth without losing a significant amount of the available signal requires reducing the central frequency of the acoustic probe signal by a factor of two. Meanwhile, imaging at twice the depth without sacrificing resolution while maintaining the same imaging frequency requires maintaining the same F-number, meaning the active aperture has to span twice as many wavelengths. Combining these two effects, the dimensions of the active aperture should be 2×2=4 times larger to maintain the same imaging resolution at twice the depth. Thus, the resolution of an array of acoustic transducer elements 222 with a 10 cm active aperture at a depth of 8 cm would be comparable to a imaging with a conventional array with a 2.5 cm acoustic aperture at a frequency of 7 MHz at a depth of 4 cm. Furthermore, by coherently summing signals from a larger number of acoustic transducer elements 222, the signal-to-noise ratio (SNR) can be increased.

Figure 7:
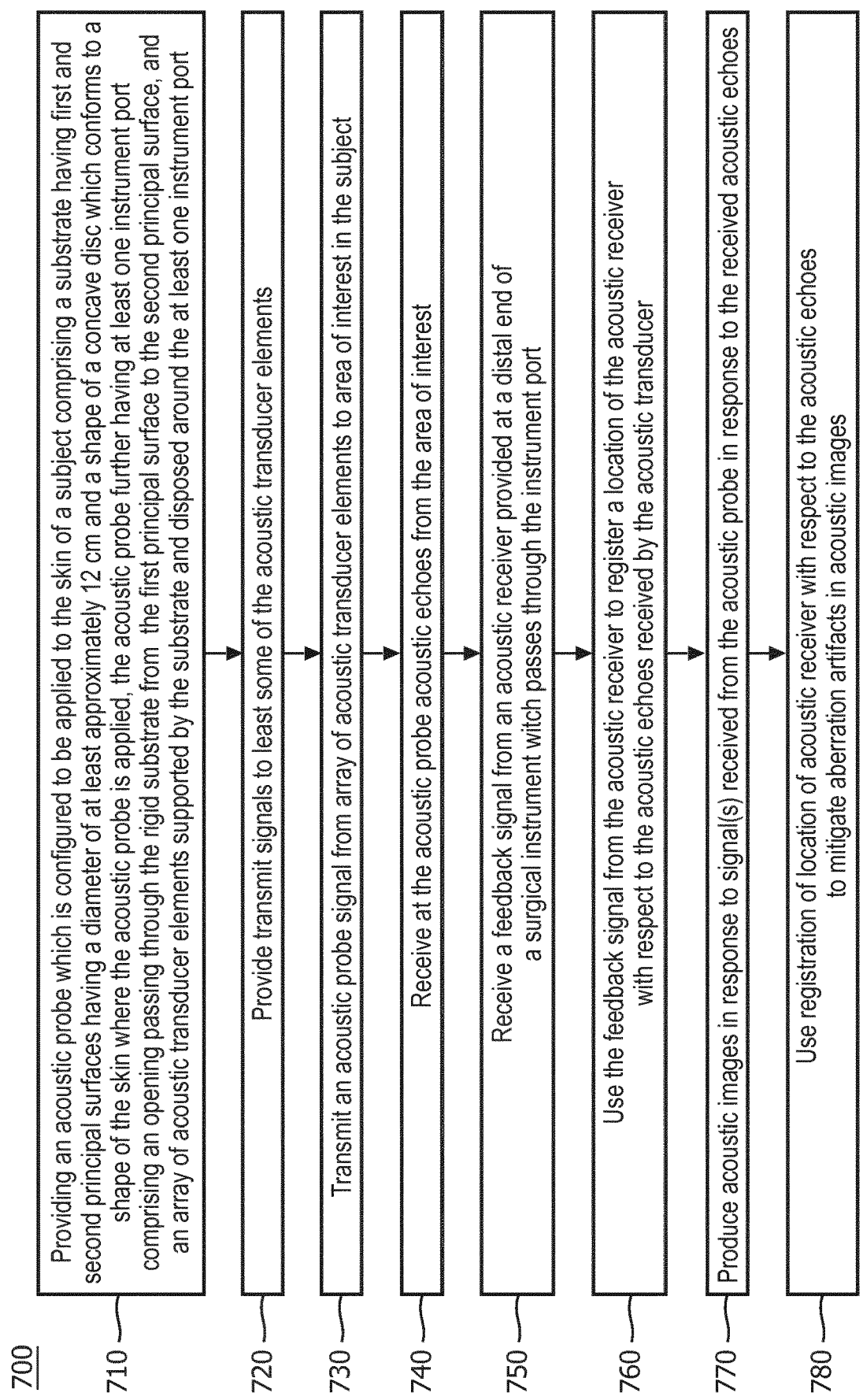
FIG. 7 illustrates a flowchart of one example embodiment of a method of acoustic imaging.

FIG. 7 illustrates a flowchart of one example embodiment of a method 700 of acoustic imaging. To provide a concrete description, reference is made to system 100 of FIG. 1 and acoustic probe 200. However, it should be understood that in general the method may be performed by a system having a different configuration than system 100, and a different configuration than acoustic probe 200 (e.g., acoustic probes 400 and 500).

An operation 710 may include providing acoustic probe 200 comprising substrate 210 which is configured to be applied to the skin of a subject, where the substrate has first and second principal surfaces 212 and 214 with a diameter of at least approximately 12 cm and a shape of a concave disc which conforms to a shape of the skin where acoustic probe 200 is applied. Here, acoustic probe 200 further has at least one device insertion port 230 comprising an opening passing through substrate 210 from first principal surface 212 to second principal surface 214, and an array of acoustic transducer elements 222 supported by substrate 210 and disposed around the device insertion port(s) 230. Acoustic probe 200 may be applied to the skin of the subject at an area where an interventional procedure is desired to be performed, and fixed in place via a strap or straps passing through attachments 240, for example with Velcro. Also, one or more interventional devices (e.g., interventional device 600) may be inserted and passed through device insertion port(s) 230 and into the tissue of the subject. In some embodiments, processor 112 may determine an orientation or alignment which will enable the interventional device passing through device insertion port 230 to reach a target location in a subject's body for an interventional procedure. In that case, before or while an interventional device is inserted into device insertion port 230, the interventional device may be aligned or oriented with the target location. Embodiments of devices and methods for such orientation or alignment will be described in greater detail below.

In an operation 720, processor 112 of acoustic imaging machine 110 may respond to user instructions received via user interface 114 and/or program instructions stored in memory to transmit signals to least some of the acoustic transducer elements 122 of acoustic probe 200.

In operation 730, in response to signals received from acoustic imaging machine 110, acoustic transducer elements 122 of acoustic probe 200 may form an acoustic probe beam and transmit the acoustic probe beam to an area of interest, for example an area in a human body where an interventional procedure is to be performed.

In an operation 740, some or all of the acoustic transducer elements 122 of acoustic probe 200 may receive acoustic echoes from the area of interest in response to the acoustic probe signal. In response to the acoustic echoes, acoustic probe 200 may transmit one or more signals to processor 112 of acoustic imaging machine 110.

In an operation 750, acoustic imaging machine 110 may receive at receiver interface 118 a feedback signal from an acoustic receiver (e.g., acoustic receiver 610) provided at a distal end of an interventional device (e.g., interventional device 600) which passes through device insertion port 230 of acoustic probe 200.

In an operation 760, acoustic imaging machine 110, and in particular processor 112, may use the feedback signal from acoustic receiver 610 to register a location of the acoustic receiver, and thus the tip of interventional device 600, with respect to the acoustic echoes received by acoustic probe 200 from the region of interest. That is, acoustic imaging machine 110 determines from the feedback signal a position of the tip of interventional device 600 so that it may track this tip and thus it may only image a small region around this tip. In other words, the acoustic imaging machine is arranged to track a relative position of the interventional device with respect to the area of interest. In some embodiments, the tracking protocol may be optimized based on the expected position of the tip of interventional device 600. For example, only a subset of transducer elements 222 may be chosen to insonify the acoustic receiver(s) 610, to ensure maximum signal on the acoustic receiver(s) 610 based on a directivity profile of acoustic receiver(s) 610. This may help increase the tracking sensitivity and SNR.

In an operation 770, acoustic imaging machine 110, and in particular processor 112, may produce acoustic images of the area of interest in response to the one or more signals received from acoustic probe 200 in response to the received acoustic echoes from the area of interest. These acoustic images including the interventional device's location may be displayed to a physician on display 116 for guiding an interventional procedure being performed by the physician in the area of interest which is being imaged.

In an operation 780, acoustic imaging machine 110, and in particular processor 112, may use the registration of the location of acoustic receiver(s) 610 with respect to the acoustic echoes to mitigate aberration artifacts in the acoustic images.

Figure 13:
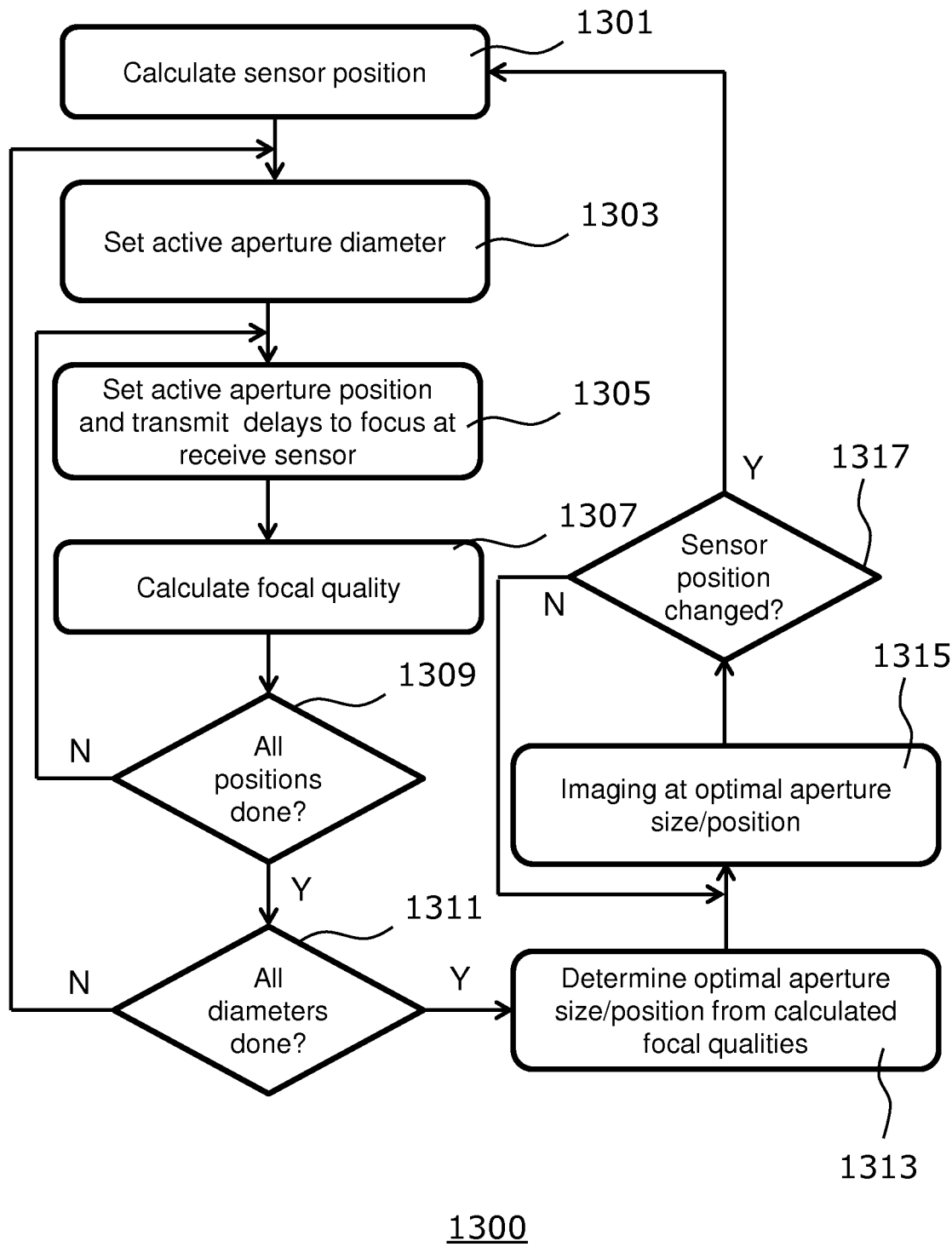
FIG. 13 is a flowchart of an active aperture optimization method according to an example embodiment.

In accordance with a preferred aspect of the present invention, the acoustic imaging machine 110 is configured to implement an optimization method 1300 of the active aperture of the acoustic probe, i.e. to select the subset of transducer elements 222 to insonify the acoustic receiver(s) 610, to ensure maximum signal on the acoustic receiver(s) 610 based on a directivity profile of acoustic receiver(s) 610 as explained above in the context of operation 760. A flowchart of an example embodiment of such an optimization method 1300 is schematically depicted in FIG. 13. The method 1300 starts in operation 1301 in which the acoustic imaging machine 110, typically processor 112, calculates the position of the acoustic receiver 610 as explained in more detail above in operation 760. This calculated position will be used by the acoustic imaging machine 110 to focus acoustic signals onto this position, as will be explained in more detail below.

In operation 1303, the acoustic imaging machine 110 defines the diameter of the active aperture, which, in case operation 1303 is performed for the first time, may equate to setting the active aperture diameter to a default value. For example, where the acoustic probe 200 has a maximum active acoustic aperture of 10 cm diameter, the initial diameter of the active acoustic aperture may be set to 3 cm and positioned in an initial position, e.g. centered around the device insertion port 230 of the acoustic probe 200, in operation 1305. It is noted that where reference is made to 'diameter' in relation to the active acoustic aperture, this is not necessarily limited to circular apertures. It is equally feasible that the selected active aperture has a polygonal shape such as a square shape in which the diameter refers to the principle diagonal of such a shape.

Furthermore, it will be understood that the selection of the size and position of the active acoustic aperture corresponds to the acoustic imaging machine 110 providing transmit signals to a selection of the acoustic transducer elements 222 to cause the selection of acoustic transducer elements 222 to transmit an acoustic probe signal to the area of interest, i.e. to cause the selection of acoustic transducer elements 222 to focus the acoustic probe signal onto the position of the acoustic receiver 610 as determined in operation 1301. This selection of acoustic transducer elements 222 defines the active acoustic aperture, and it will be understood that adjustments to the active acoustic aperture in terms of change of diameter and/or change of position corresponds to a change in the acoustic transducer elements that are selected to form the active acoustic aperture. This is further explained with the aid of FIG. 14, which schematically depicts the acoustic probe 200 having an active acoustic aperture 225 formed of a selected plurality of acoustic transducer elements 222 (not shown in FIG. 14 for the sake of clarity only).

Upon defining the initial position of the active acoustic aperture 225 in operation 1305, here schematically depicted by situation A in which the active acoustic aperture 225 is centred around the device insertion port 230 by way of non-limiting example, the acoustic imaging machine 110 controls the acoustic transducer elements 222 defining the active acoustic aperture 225 to cause the selection of acoustic transducer elements to transmit an acoustic probe signal in the direction of the acoustic receiver 610, for example to focus the acoustic probe signal onto or over a small surrounding area of the acoustic receiver 610 to get an indication of the focal point quality, for example by measuring a point spread function of the system by sampling some points in close vicinity to the focal point. As the acoustic receiver position is fixed, this may be accomplished by multiple ultrasound transmit events involving systematic beam steering or translation of the acoustic aperture 225. Alternatively, the acoustic aperture 225 may be focussed at the acoustic receiver 610, and the time duration over which acoustic signal is received may be determined. A time window much larger than the transmit pulse length indicates increased abberation.

In operation 1307, a feedback signal is received by the acoustic imaging machine 110, which feedback signal originates from the acoustic receiver 610 and is a response signal to the acoustic probe signal directed at the acoustic receiver 610 with the acoustic transducer elements 222 defining the selected active acoustic aperture 225 as generated in operation 1305.

The acoustic imaging machine 110 determines a quality indication of the feedback signal in operation 1307, which quality indication in some embodiments may be the determination of the focal point quality of the transmit signals directed by the selection of acoustic transducer elements 222 defining the active acoustic aperture 225 onto the acoustic receiver 610. Such a focal point quality may be determined using any suitable metric, as is well-known per se to the person skilled in the art. The metric deployed by the acoustic imaging machine 110 may differ depending on the clinical application for which the acoustic probe 200 is used. For example, in a scenario in which it is desirable to minimize sidelobe energy, for instance because small hypo-echoic features are of interest, a different metric may be used compared to a scenario in which it is desirable to maximize main lobe definition, for instance because small hyperechoic features need to be resolved.

Figure 14:
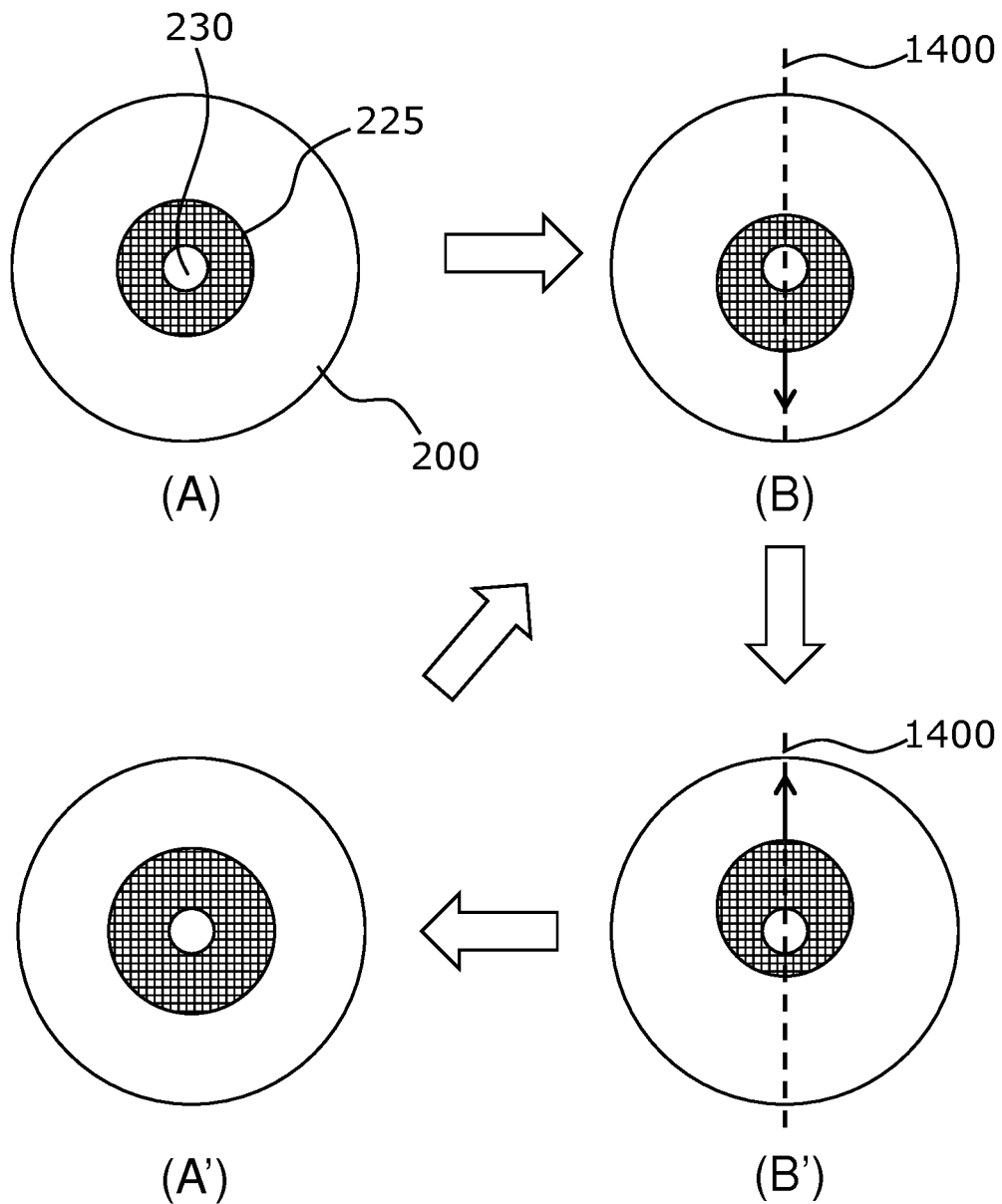
FIG. 14 schematically depicts example stages of the active aperture optimization method as deployed to an acoustic probe.

Subsequent operation 1309 is an optional operation, which for example may be deployed if the active acoustic aperture 225 with the chosen diameter is to be translated in one or more directions across the surface 214 carrying the acoustic transducer elements 222 in order to relocate the active acoustic aperture 225 on this surface, i.e. by selecting a different set of acoustic transducer elements 222 to define the active acoustic aperture 225 in this new location, as schematically depicted by situation B in FIG. 14. This operation therefore may be used to find the optimal location of the active acoustic aperture 225 relative to the interventional device 600 as determined through its acoustic receiver 610. Specifically, it may be checked in operation 1309 if all predefined locations to be tested have been tested. If this is not the case, the method 1300 may revert back to operation 1305 in which the active aperture position is redefined in accordance with a position adjustment algorithm or schedule, after which a quality indication of the feedback signal for this adjusted active acoustic aperture 225 is determined. This is repeated until all positions or locations of the active acoustic aperture 225 have been investigated in this manner. This is schematically depicted in FIG. 14 by situations B and B', which depict the repositioning of the active acoustic aperture 225 along the axis 1400. For example, the active acoustic aperture 225 may be systematically repositioned using fixed step increments over a fixed distance range, e.g. 0.4 mm increments over a 10 mm range on either side of the initial position of the active acoustic aperture 225, thereby leading to a total of 51 measurement points.

As will be understood by the skilled person, in the above example, the initial positioning of the active acoustic aperture 225 centered around the device insertion port 230 is by way of non-limiting example only as the initial position of the active acoustic aperture 225 may be chosen in any suitable location on the axis 1400. Moreover, it is noted that the investigation of the ideal position of the active acoustic aperture 225 is not limited to the systematic repositioning of the active acoustic aperture 225 in a single direction; systematic variation of this position in multiple directions, e.g. in a second direction perpendicular to the axis 1400 equally may be deployed.

Additionally or alternatively, the active acoustic aperture 225 may be repositioned relative to the acoustic receiver 610 using electronic beam steering, such that with a single selection of acoustic transducer elements 222 a plurality of (focal) quality measurements with the acoustic receiver 610 is performed, with each quality measurement corresponding to a particular beam steering angle (or range of beam steering angles), in which case this particular beam steering angle (or range of angles) is systematically varied in order to obtain the optimal positioning of the active acoustic aperture 225 relative to the acoustic receiver 610. In this manner, instrument tracking capability may be optimized.

In operation 1311, it is checked if all diameters of the active acoustic aperture 225 have been investigated in case this diameter is to be systematically varied. For example, for an acoustic probe 200 having an intrinsic active acoustic aperture of approximately 10 cm as defined by the total number of acoustic transducer elements 222, the effective diameter of the active acoustic aperture 225, i.e. the diameter at which the active acoustic aperture 225 exhibits optimal acoustic performance, may be found by systematically varying the size of this diameter in this calibration method 1300, as is schematically depicted by situation A' in FIG. 14. This for instance may be done by systematically increasing or decreasing the size of the diameter from an initial value using fixed increments. By way of non-limiting example, for the above acoustic probe 200, an initial diameter size value may be set to 3 cm and may be systematically incremented by 1 cm until the diameter has reached a size of 10 cm. If it is found in operation 1311 that not all diameters have been investigated yet, the method 1300 may revert back to operation 1303 in which the diameter of the active acoustic aperture 225 is adjusted accordingly, after which the above explained acoustic quality measurements using the feedback signal from the acoustic receiver 610 are performed for the active acoustic aperture 225 with the adjusted diameter.

Once all desired acoustic quality measurements have been collected, e.g. stored in a data storage device such as a memory, the method 1300 proceeds to operation 1313 in which the size and/or position of the active acoustic aperture 225 having the optimal acoustic performance is determined from the collected acoustic quality measurements, after which the method 1300 may proceed to operation 1315 in which imaging of the area of interest with the interventional device 600 in situ is performed with the acoustic imaging machine 110 is configured to operate the acoustic probe 200 such that the acoustic imaging machine 110 transmits further signals to the preferred selection of the acoustic transducer elements 222, i.e. the selection of acoustic transducer elements 222 defining the optimal active acoustic aperture 225 to cause the preferred selection of acoustic transducer elements 222 to transmit a further acoustic probe signal to the area of interest and produce acoustic images of the area of interest from acoustic echoes received by the acoustic probe 200 from the area of interest in response to said further acoustic probe signal. This may be continued until the interventional device 600 is repositioned within the area of interest, as it is checked in operation 1317. Upon such a repositioning, the optimal active acoustic aperture 225 needs to be recalculated as this aperture is a function of the position (e.g. insertion depth) of the interventional device 600 into the area of interest. Consequently, upon such a repositioning, the method 1300 may revert back to operation 1301 to determine the optimal active acoustic aperture 225 for the new position of the interventional device 600.

At this point, it is noted that the above described embodiment of the aperture calibration method 1300 is an example embodiment only. For instance, it is equally feasible to only optimize the size of the active acoustic aperture 225 or to only optimize the position of the active acoustic aperture 225, for example by moving the active acoustic aperture 225 having a fixed size along a range of positions on the transducer array.

It furthermore should be understood that the repositioning of the active acoustic aperture 225, either in isolation or in combination with resizing the active acoustic aperture 225, is not limited to systematic repositioning of the active acoustic aperture 225 long one or more axes 1400. Such repositioning may be achieved in any suitable manner. For example, the active acoustic aperture 225 may be repositioned in a systematic manner to obtain a Cartesian grid or to form concentric circles around the device insertion port 630 or to form concentric circles in terms of focal points around the acoustic receiver 610. In another embodiment, a synthetic aperture technique may be deployed in which the array of acoustic transducer elements 222 is divided into a plurality of sub-apertures, wherein for each sub-aperture 225 the acoustic performance, e.g. in terms of focal quality, is determined by sliding or steering the acoustic signals of the sub-aperture 225 over a region surrounding the acoustic receiver 610. In this manner, well-performing sub-apertures 225 may be identified, after which the method 1300 may resize the thus identified sub-apertures 225 by clustering them with neighboring sub-apertures. In this manner, a range of aperture sizes may be evaluated, from which the best performing aperture may be selected as explained above.

Moreover, embodiments of the method 1300 are not limited to systematic variation of the size and/or position of the active acoustic aperture 225 to focus acoustic signals on the acoustic receiver 610. It is equally feasible to move the transmit focus generated with such an active acoustic aperture 225 over a limited depth range within the area of interest to further expand the systematic evaluation of the optimal active acoustic aperture 225 of the acoustic probe 200 for a particular position of the interventional device 600 within the area of interest.

As noted above, one desirable attribute for an acoustic imaging system and method is hands free operation of the acoustic probe. In particular, when using ultrasound imaging to guide one or more interventional devices (e.g., surgical tools) in a minimally invasive surgical procedure, hands free operation of the acoustic probe is desired so that a sonographer is not needed in addition to the physician/surgeon. However, during a procedure there may however be a moment where the surgeon that is holding the interventional device at the desired location wants or needs to use her/his hands for a different task without disturbing the position of the interventional device. This could for example involve manipulating the position of a second interventional device, manipulating settings on the imaging machine, or inserting a guidewire.

Figure 8:
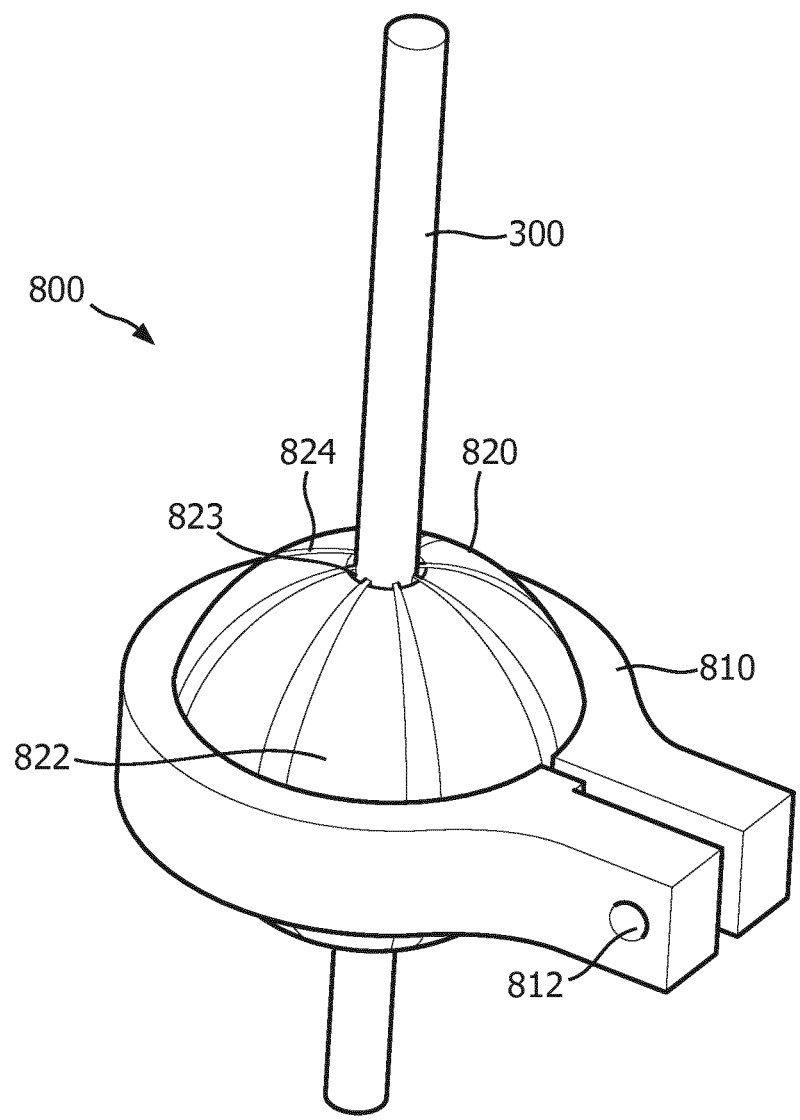
FIG. 8 illustrates an example embodiment of an instrument guide for a device insertion port of an acoustic probe.

To this end, FIG. 8 illustrates an example embodiment of an instrument guide 800 for a device insertion port (e.g., device insertion port 230) of an acoustic probe (e.g., acoustic probe 200).

Figure 9:
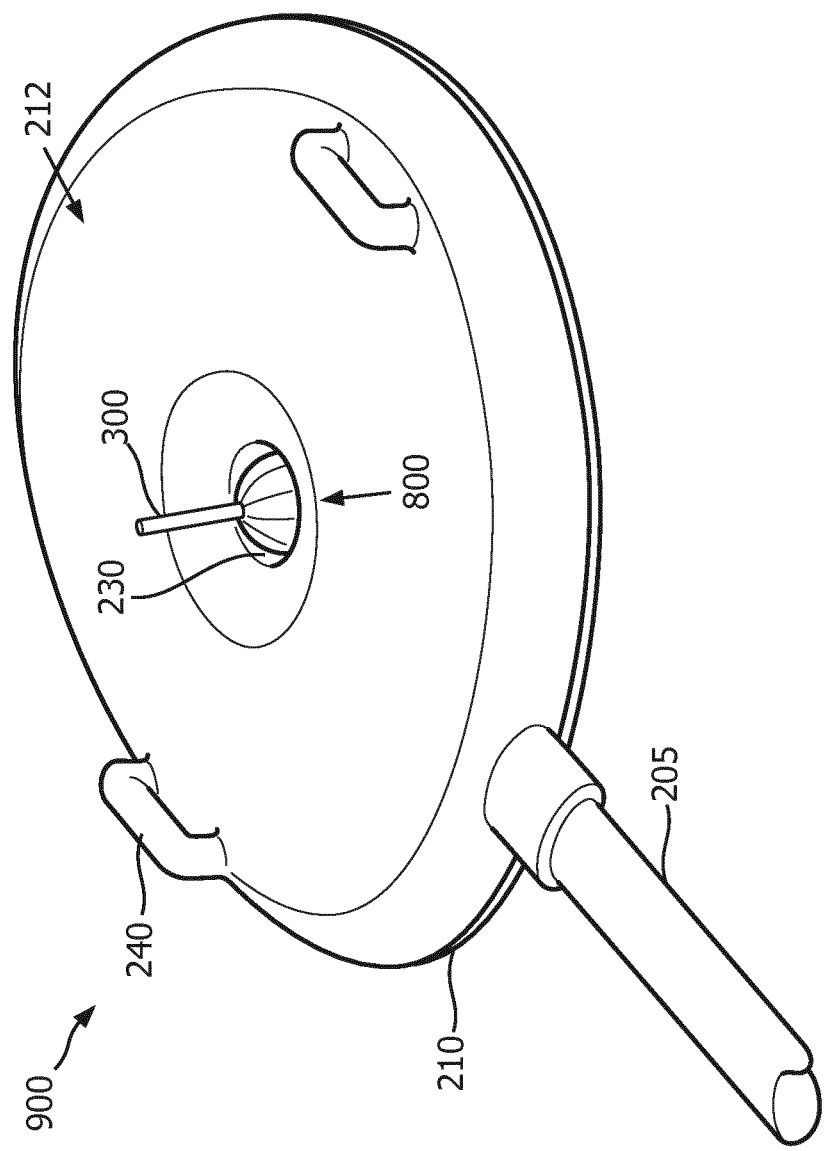
FIG. 9 illustrates an example arrangement of an acoustic probe with a device insertion port and an instrument guide disposed in the device insertion port.

FIG. 9 illustrates an example embodiment of an arrangement 900 of acoustic probe 200, instrument guide 800 disposed in device insertion port 230, and interventional device 300 disposed to pass through instrument guide 800. It should be understood that similar arrangements can be provided for acoustic probes 400 and 500, and for other acoustic probes with different configurations of one or more device insertion ports. It should also be understood, that instrument guide 800 may be integrated with acoustic probe 200 and therefore considered to be part of the acoustic probe, or may be a separate element which is removably inserted in device insertion port 230.

Instrument guide 800 comprises: a ball structure 820 having a cylindrical hole 823 for interventional device 300 to pass therethrough; and an adjustable clamp 810 which at least partially surrounds ball structure 820. Clamp 810 has a spherical interior surface and is mounted to an interior surface of device insertion port 230.

In some versions, cylindrical hole 823 has a diameter which allows an interventional device 300 having a diameter of at least about 1.5 mm to pass therethrough. Ball structure 820 may include a plurality of larger semi-soft deformable segments 822, and smaller rigid segments 824. In some versions, segments 822 may be made out of porous Teflon, and segments 824 be made out of stainless steel. Beneficially, adjustable clamp 810 has a spherical inside surface, with a loose enough fit such that ball structure 820 may rotate freely and interventional device 300 may freely slide in and out of instrument guide 800.

In operation, instrument guide 800 allows free movement of interventional device 300 which is inserted therein until it is put in locking mode by a locking unit and when locked then interventional device 300 is securely held in place (at a fixed position).

More specifically, when adjustable clamp 310 is loosened then ball structure 820 can rotate freely within adjustable clamp 810 and an insertion depth of interventional device 300 within instrument guide 800 may be adjusted. However, when adjustable clamp 810 is tightened then ball structure 820 is immobilized within adjustable clamp 810 and an insertion depth of interventional device 300 within instrument guide 800 is locked.

To lock interventional device 300 in instrument guide 800, adjustable clamp 810 may be squeezed together from the protruding ends where thru holes 812 are located. In various embodiments, this could for example be achieved with a nut/bolt structure, a mechanism similar to that employed with a bicycle cable, an electromagnetic actuator, etc. When adjustable clamp 810 is squeezed, it locks ball structure 820 in place, and also pushes segments 824 against interventional device 300 to lock the insertion depth.

In some embodiments, a foot pedal may be employed by a user (e.g., physician/surgeon) to selectively tighten and loosen adjustable clamp 810 to lock and unlock instrument guide 800. In other embodiments, acoustic imaging machine 110 may respond to a voice command from the user to selectively tighten and loosen adjustable clamp 810 to lock and unlock instrument guide 800. In still other embodiments, locking of adjustable clamp 810 may be initiated by an acoustic (ultrasound) scanner, to avoid locking the interventional device in certain critical areas.

Many variations and different embodiments of an instrument guide and an acoustic probe including an instrument guide are possible.

In some embodiments the shape and/or dimensions of the hole in the instrument guide may be adapted to the shape and/or if a particular interventional device to be inserted.

In some embodiments, an instrument guide may be fixed in place by magnetizing it with an electromagnet.

In some embodiments, an acoustic probe may have multiple instrument ports and some or all of the instrument ports may be equipped with an instrument guide.

In some embodiments, an instrument guide may include a disposable ball structure, to aid in maintaining sterility in a surgical environment.

In some embodiments, an instrument guide may be configured to provide separate, independent, locking of the orientation or direction of the hole in the instrument guide in which the interventional device is inserted, and locking of the interventional device inserted within the hole.

When inserting an interventional device inserted within an instrument guide in device insertion port of an acoustic probe, it may be challenging to determine the correct orientation or angulation needed for an interventional device to reach a certain anatomical target location in the acoustic image.

Accordingly, described below is a system and acoustic probe which includes a device insertion port and an encoded and adjustable instrument guide which can communicate with an acoustic imaging machine to automatically determine the optimal insertion orientation for the interventional device, and a method to automatically or manually optimize the orientation of the instrument guide so that an interventional device inserted through the instrument guide in that orientation will intersect with a user-defined target anatomical location in the acoustic image. This can reduce the incidence of repeated device insertions, thus reducing trauma to the subject, improving the clinical workflow, and enabling more accurate interventions.

Figure 10:
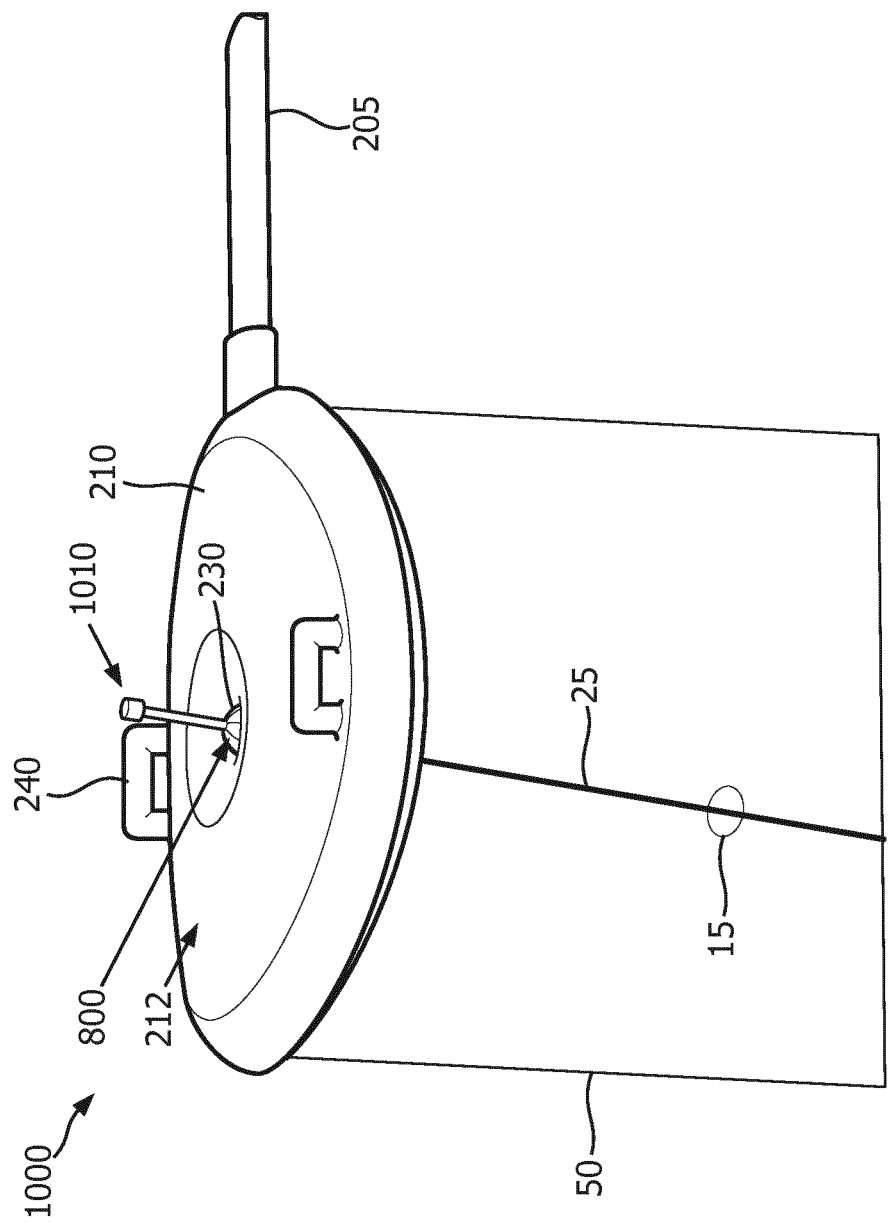
FIG. 10 illustrates an example operation of orienting an instrument guide disposed in a device insertion port of an acoustic probe to position an interventional device tip at a desired location.

FIG. 10 illustrates an example operation of orienting an instrument guide disposed in a device insertion port of an acoustic probe to position an interventional device tip at a desired target location within an area of interest which is being acoustically imaged in a subject. To provide a concrete description, reference is made to system 100 of FIG. 1 and arrangement 1000, which is a combination of acoustic probe 200, instrument guide 800 and a joystick 1010. However, it should be understood that in general the operation may be performed by an arrangement having a different configuration than arrangement 1000, and a different configuration than acoustic probe 200 (e.g., acoustic probes 400 and 500).

FIG. 10 shows an acoustic imaging plane 50 and a joystick 1010 which may be used for maneuvering instrument guide 800 to a desired orientation which may have been computed by processor 112 of acoustic imaging machine 110 to place the tip of an interventional device at a target location 15.

In operation, once acoustic probe 1000 has been satisfactorily positioned on the subject of an interventional procedure, then a clinician/surgeon may define target location 15 within the area of interest of acoustic image plane 50, for example, by clicking a point or drawing a target location or region on an ultrasound image via user interface 114 and display 118. Processor 112 may then retrieve target location 15 from the acoustic scanner. Since instrument guide 800 is attached to, and hence, registered to, the array of acoustic transducer elements 222 of acoustic probe 200, processor 112 may automatically compute the orientation of instrument guide 800 which is needed to enable the interventional device 300 to reach target area 15.

In some embodiments, the orientation of instrument guide 800 may be defined by an encoder provided with instrument guide 800.

In one embodiment of an encoder, ball structure 820 may have a unique spatially varying optical pattern provided (e.g., painted) on it which may be read out using a high resolution miniature camera embedded in adjustable clamp 810. Such pattern may, for example, be a grid of latitude and longitude lines with line thicknesses depending on longitude and latitude coordinates. For further differentiation the longitude lines may also have a different color then the latitude lines. Such an arrangement may provide three degrees of freedom (i.e., tip/tilt/rotation) for moving ball structure 820. In that case, processor 112 may calculate the desired orientation of instrument guide 800 and associated encoder value(s), and may automatically maneuver instrument guide 800 to have the calculated orientation via feedback by comparing the actual encoder value(s) to the calculated encoder value(s). In some embodiments, this may be done before the interventional device is introduced through instrument guide 800. Electronic communication between processer 112 and instrument guide 800 may be enabled using wired connections that can be included in probe cable 205. Once instrument guide 800 has been adjusted to the desired orientation, the interventional device may be inserted as needed.

Some embodiments may utilize additional encoding for the process of inserting interventional device at target location 15 in the subject. For example, in some embodiments the interventional device may have one or more length markers as well as small grooves for length approximation and locking the interventional device. Length and angle measurements based on these length marker(s) and/or small grooves may be used for approximating the orientation and position of the interventional device.

In another embodiment, processor 112 may calculate the desired orientation of instrument guide 800 and associated encoder value(s), and the user may manually maneuver instrument guide 800 (e.g., via joystick 1010) to match the calculated encoder value(s).

To aid in manual adjustment of instrument guide 800, joystick 1010 may be temporarily attached to instrument guide 800. Once the orientation/adjustment process is complete, joystick 1010 can be removed and replaced by the interventional device. In another embodiment, joystick 1010 may have a hollow channel through which the interventional device may be inserted, which may allow the interventional procedure to be performed without having to remove joystick 1010. Alternatively, joystick 1010 may be permanently attached to instrument guide 800 in an aligned orientation, but translated slightly relative to the insertion point of the interventional device to allow insertion of the interventional device.

During manual adjustment of instrument guide 800, a projected tool path 25 may be displayed on display device 118 and may be continuously updated so that the user can also use this as feedback to correctly align instrument guide 800. In some cases, if the required adjustments are out of image plane 50, it may not be possible to use only image-based feedback to align instrument guide 800.

Figure 11:
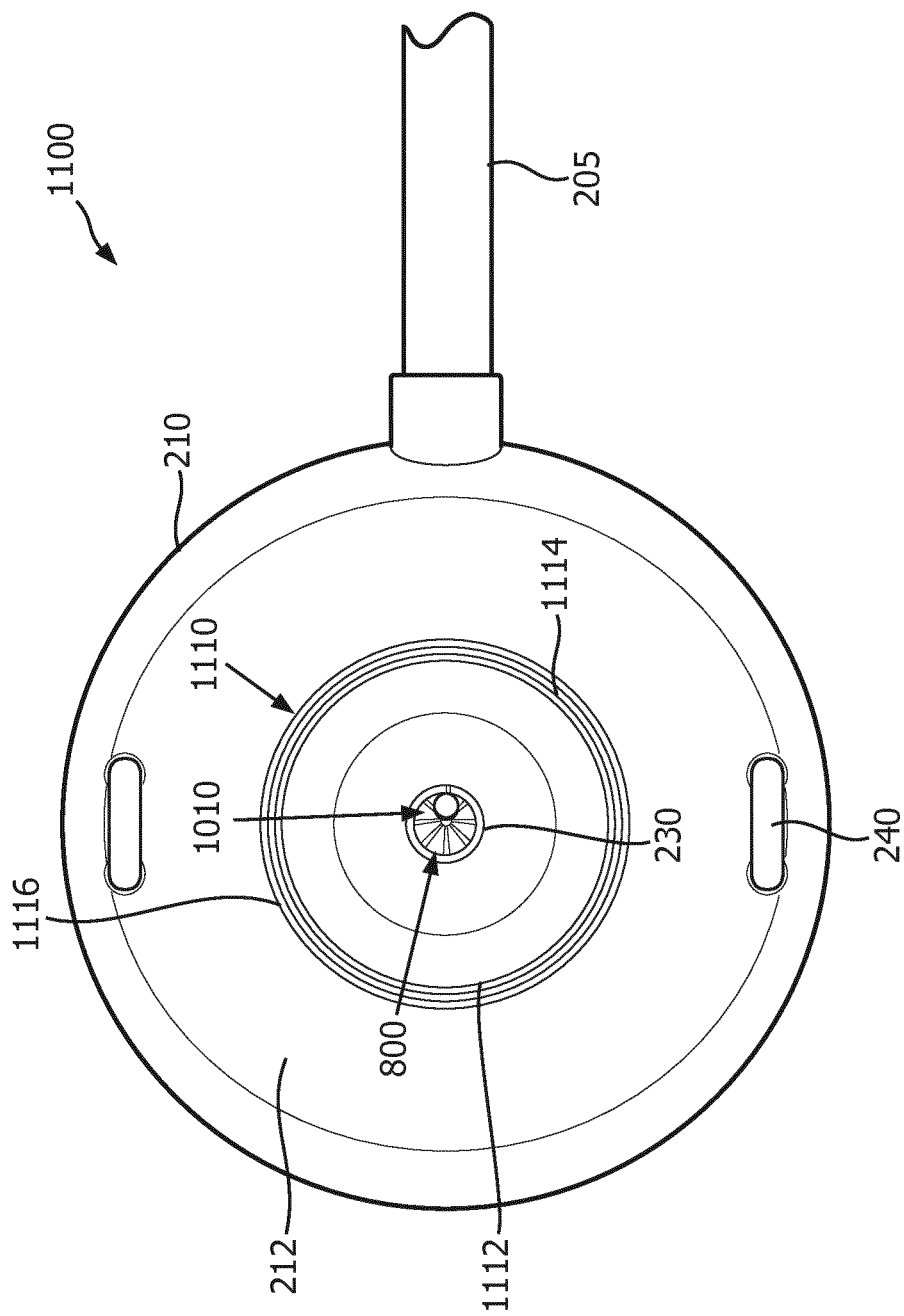
FIG. 11 illustrates yet another example embodiment of an acoustic probe with a device insertion port and an instrument guide disposed in the device insertion port.

To aid in out-of-plane adjustments, FIG. 11 illustrates yet another example embodiment of an acoustic probe 1100 with device insertion port 230 and instrument guide 800 disposed in device insertion port 230. The upper surface of substrate 210 of acoustic probe 1100, surrounding device insertion port 230, is fitted with three circular concentric rings of light elements (e.g., light emitting diodes (LEDs)) 1100 of different colors. For example, in some embodiments an innermost ring 1112 of LEDs may be yellow, a middle ring 114 may be green, and an outermost ring 1116 may be red. These LED lights may serve as guidance while the user is maneuvering instrument guide 800 to a desired orientation in device insertion port 230. In some embodiments, at any given time only one LED may be illuminated to indicate a direction in which the user should maneuver instrument guide 800.

Figure 12:
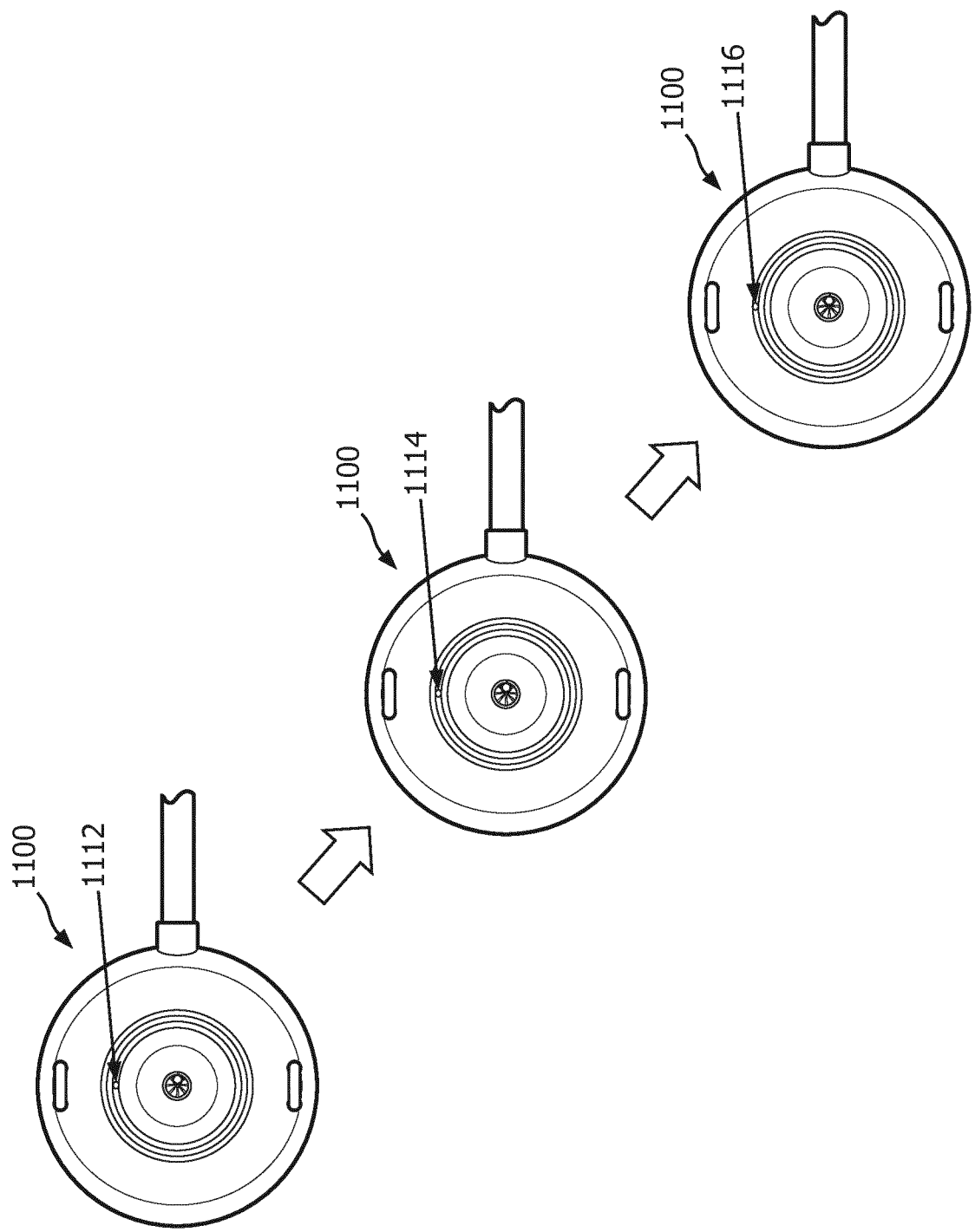
FIG. 12 illustrates a process of providing user feedback while orienting an instrument guide disposed in a device insertion port of an acoustic probe to position an interventional device tip at a desired location.

FIG. 12 illustrates a process of providing user feedback while orienting instrument guide 800 disposed in device insertion port 230 of acoustic probe 1100 to position an interventional device tip at desired location 15.

Once processor 112 calculates the encoder value(s) for instrument guide 800, an LED for indicating the appropriate orientation may be activated as follows. First, a yellow LED of innermost ring 1112 in the determined direction may be activated, indicating to the user that the instrument guide 800 needs to be pivoted in that direction. Once the user has pivoted instrument guide 800 by the correct amount as determined by processor 112, the yellow LED of innermost ring 1112 may be deactivated and a green LED of middle ring 1114 may be activated, indicating that instrument guide 800 is in the optimal orientation as determined by processor 112. If the user overshoots the target and pivots instrument guide 800 too much, then the green LED of middle ring 1114 may be deactivated and a red LED of outermost ring 1116 may be activated, indicating that the user has pivoted instrument guide 800 too much. Optionally, at this stage, a yellow LED in the diametrically opposite location may also be activated, indicating that the user has to now pivot instrument guide 800 back in the opposite direction to reach the optimal orientation.

As in the case of automatic orientation of instrument guide 800 by processor 112, once instrument guide 800 has been adjusted to the desired orientation, instrument guide 800 may be held steady in the desired orientation as described above, and the interventional device may be inserted as needed.

In some embodiments, the LED-based workflow described above with respect to FIG. 12 may be used for coarse adjustment of the orientation of instrument guide 800, and the current encoder values (and the desired optimal encoder values) may also be displayed display 118 to allow the user to further fine-tune the orientation of instrument guide 800, if needed. In some embodiments, acoustic imaging machine 110 may provide audio feedback (for example, a beep) to a user to indicate that the optimal orientation of instrument guide 800 has been reached.

Depending on the shape of the device insertion port containing instrument guide 800, instrument guide 800 may be adjusted in multiple ways with different available degrees of freedom (DOF) for maneuvering an interventional device inserted through it.

For example, in embodiments where instrument guide 800 only can be tipped and tilted (pitch and yaw), but is not translatable, within the device insertion port (e.g., device insertion port 230), then there will be 4 DOF for maneuvering the interventional device.

In other embodiments where instrument guide 800 can be translated along one axis (e.g., device insertion port 430 or 539), then there will be 5 DOF for maneuvering the interventional device.

In yet other embodiments where instrument guide 800 can be translated along two perpendicular axis (e.g., the device insertion port is an X-shaped slit or slot), then there will be 6 DOF for maneuvering the interventional device.

In some embodiments, tracking of the interventional device along the path of insertion 25 can be accomplished using acoustic (e.g., ultrasound) tracking (InSitu), in which one or more acoustic sensors on the shaft of the interventional device are tracked within the acoustic images. The extent of insertion of the interventional device within the instrument guide can also be quantified using an encoder on the instrument guide, for example using length markers described above. While this method will not account for any bending of the interventional device, it can serve as a good initial approximation for the position of the tip of the interventional device, which then may be utilized by other tracking methods such as InSitu.

While preferred embodiments are disclosed in detail herein, many variations are possible which remain within the concept and scope of the invention. Such variations would become clear to one of ordinary skill in the art after inspection of the specification, drawings and claims herein. The invention therefore is not to be restricted except within the scope of the appended claims.

The invention claimed is:

1. An ultrasound system for providing images of an area of interest comprising:
   an acoustic probe having:
      a substrate having first and second principal surfaces, and further having at least one device insertion port comprising an opening passing through the substrate from the first principal surface to the second principal surface, said opening suitable for insertion of an interventional device, and an array of acoustic transducer elements supported by the substrate and defining an active area of the substrate, said array disposed around the at least one device insertion port; and an acoustic imaging machine connected to the acoustic probe and configured to:

perform a calibration of the acoustic probe to obtain acoustic images of the area of interest, wherein the calibration comprises:

systematically varying a selection of the acoustic transducer elements through a plurality of predefined selections of the acoustic transducer elements, wherein each selection of the plurality of predefined selections defines a different respective active aperture of the acoustic probe, wherein at least one of an amount that a center of the respective active aperture is offset from the at least one device insertion port or a distance between an outer edge of the respective active aperture and the at least one device insertion port varies between the plurality of predefined selections, and, for each selection of the plurality of predefined selections:

providing transmit signals to the selection of the acoustic transducer elements to cause the selection of acoustic transducer elements to transmit an acoustic probe signal to the area of interest; and recording a feedback signal of the transmit signals from an acoustic receiver provided at a distal end of the interventional device that is passed through the at least one device insertion port into the area of interest;

evaluating the recorded feedback signals using a metric for assessing a focal point quality of the acoustic probe signals transmitted to the acoustic receiver; and identifying, based on the evaluation of the recorded feedback signals, a preferred selection of the acoustic transducer elements from among the plurality of predefined selections;

transmit, based on the calibration, further signals to the preferred selection of the acoustic transducer elements to cause the preferred selection of acoustic transducer elements to transmit a further acoustic probe signal to the area of interest; and produce the acoustic images of the area of interest from acoustic echoes received by the acoustic probe from the area of interest in response to said further acoustic probe signal.

2. The ultrasound system of claim 1, wherein the acoustic imaging machine is configured to systematically vary the selection of the acoustic transducer elements through the plurality of predefined selections by repeatedly:

systematically varying a location of the active aperture having a defined size; and redefining the size of the active aperture based on a defined range of sizes for the acoustic aperture until each size in said defined range of sizes has been used.

3. The ultrasound system of claim 1, wherein the acoustic imaging machine is further configured to systematically vary a beam steering angle for each selection of the of the acoustic transducer elements through the plurality of predefined selections during the systematic variation of the selection of the acoustic transducer elements.

4. The system of claim 1, wherein the acoustic imaging machine is further configured to use the feedback signal from the acoustic receiver to register a location of the acoustic receiver with respect to the acoustic echoes received by the acoustic probe.

5. The system of claim 4, wherein the acoustic imaging machine further comprises a processor arranged to mitigate aberration artifacts in the acoustic images based on the registered location of the acoustic receiver.

6. The system of claim 1, wherein the substrate has a shape of a concave disc, and wherein the active area of the substrate defined by the array of acoustic transducer elements has a diameter of at least 12 cm.

7. A method for providing images of an area of interest comprising:

providing an acoustic probe comprising:

a substrate configured to be applied to the skin of a subject, the substrate having first and second principal surfaces and further having at least one device insertion port comprising an opening passing through the substrate from the first principal surface to the second principal surface, and an array of acoustic transducer elements supported by the substrate and disposed around the at least one device insertion port;

performing a calibration of the acoustic probe to obtain acoustic images of the area of interest, wherein the performing the calibration comprises:

systematically varying a selection of the acoustic transducer elements through a plurality of predefined selections of the acoustic transducer elements, wherein each selection of the plurality of predefined selections defines a different respective active aperture of the acoustic probe, wherein at least one of an amount that a center of the respective active aperture is offset from the at least one device insertion port or a distance between an outer edge of the respective active aperture and the at least one device insertion port varies between the plurality of predefined selections, and, for each selection of the plurality of predefined selections:

providing transmit signals to the selection of the acoustic transducer elements to cause the selection of acoustic transducer elements to transmit an acoustic probe signal to the area of interest; and recording a feedback signal of the transmit signals from an acoustic receiver provided at a distal end of an interventional device that is passed through the at least one device insertion port into the area of interest;

evaluating the recorded feedback signals using a metric for assessing a focal point quality of the acoustic probe signals transmitted to the acoustic receiver;

identifying, based on the evaluation of the recorded feedback signals, a preferred selection of the acoustic transducer elements from among the plurality of predefined selections; and transmitting, based on the calibration, further signals to the preferred selection of the acoustic transducer elements to cause the preferred selection of acoustic transducer elements to transmit a further acoustic probe signal to the area of interest; and producing the acoustic images of the area of interest from acoustic echoes received by the acoustic probe from the area of interest in response to said further acoustic probe signal.

8. The method of claim 7, wherein systematically varying the selection of the acoustic transducer elements through the plurality of predefined selections comprises repeatedly:

systematically varying a location of the active aperture having a defined size; and redefining the size of the active aperture based on a defined range of sizes for the acoustic aperture until each size in said defined range of sizes has been used.

9. The method of claim 7, further comprising systematically varying a beam steering angle for each selection of the of the acoustic transducer elements through the plurality of predefined selections during the systematic variation of the selection of the acoustic transducer elements.

10. The method of claim 7, further comprising:

using the feedback signal from the acoustic receiver to register a location of the acoustic receiver with respect to the acoustic echoes received by the acoustic probe; and using the registration of the location of the acoustic receiver with respect to the acoustic echoes to mitigate aberration artifacts in the acoustic images.

11. The method of claim 7, further comprising repeating the calibration in response to a change in position of the interventional device within the area of interest.

12. The system of claim 1, further comprising the interventional device.

* * * * *